US011084855B2

(12) United States Patent
Nold et al.

(10) Patent No.: US 11,084,855 B2
(45) Date of Patent: Aug. 10, 2021

(54) IL-37 VARIANTS

(71) Applicants: Monash University, Clayton (AU); Hudson Institute of Medical Research, Clayton (AU)

(72) Inventors: Marcel Nold, Clayton (AU); Claudia Nold, Clayton (AU); Andrew Ellisdon, Clayton (AU); James Whisstock, Clayton (AU)

(73) Assignees: Monash University, Clayton (AU); Hudson Institute of Medical Research, Clayton (AU)

( * ) Notice: Subject to any disclaimer, the term of this patent is extended or adjusted under 35 U.S.C. 154(b) by 0 days.

(21) Appl. No.: 15/737,204

(22) PCT Filed: Jun. 15, 2016

(86) PCT No.: PCT/AU2016/050495
§ 371 (c)(1),
(2) Date: Dec. 15, 2017

(87) PCT Pub. No.: WO2016/201503
PCT Pub. Date: Dec. 22, 2016

(65) Prior Publication Data
US 2018/0162918 A1 Jun. 14, 2018

(30) Foreign Application Priority Data

Jun. 15, 2015 (AU) .............................. 2015902262
Feb. 26, 2016 (AU) .............................. 2016900703

(51) Int. Cl.
*A61K 38/20* (2006.01)
*A61K 38/00* (2006.01)
*C07K 14/54* (2006.01)
*A61P 29/00* (2006.01)

(52) U.S. Cl.
CPC .............. *C07K 14/54* (2013.01); *A61P 29/00* (2018.01); *A61K 38/00* (2013.01)

(58) Field of Classification Search
CPC .......... A61K 38/20; A61P 29/00; C07K 14/54
See application file for complete search history.

(56) References Cited

U.S. PATENT DOCUMENTS

| | | |
|---|---|---|
| 4,518,584 A | 5/1985 | Mark et al. |
| 4,737,462 A | 4/1988 | Mark et al. |
| 5,424,398 A | 6/1995 | Middeldorp et al. |
| 7,033,783 B2 | 4/2006 | Sims et al. |
| 2003/0148467 A1 | 8/2003 | West et al. |

FOREIGN PATENT DOCUMENTS

| | | |
|---|---|---|
| CN | 104083755 A | 10/2014 |
| WO | WO-0024899 A2 | 5/2000 |
| WO | 2012024302 A2 | 2/2012 |

OTHER PUBLICATIONS

Yan, G., et al. Genome sequenceing an comparison of two nonhuman primate animal models, the cynomolgus and Chinese rhesus macaques. Nature Biotechnology, 2011, vol. 29, p. 1019-1023.*
Wilson, R.K, et al. "A 6x draft sequence assembly of the Pongo pygmaeus abelii genome."; Submitted to the EMBL/GenBank/DDBJ databases, Feb. 2008.*
Pan et al. "IL-1H, An Interleukin 1-Related Protein that Binds IL-18 Receptor/IL-1Rrp", Cytokine, Jan. 7, 2001, 13 (1):1-7.
International Search Report for International PCT Application No. PCT/AU2016/050495, dated Aug. 31, 2016, 5 pages.
Written Opinion of the International Searching Authority for International PCT Application No. PCT/AU2016/050495, dated Aug. 31, 2016, 7 pages.
Bricogne et al. (Dec. 19, 2017) "BUSTER Stable Release," Global Phasing Limited. 2(10):1-48.
Cavalli et al. (2017) "Suppression of inflammation and acquired immunity by IL-37," Immunological Reviews. 281:179-190.
UniProt Consortium (Jul. 27, 2011) "Interleukin-1: IL37," UniProt Accession No. F6U119. 5 pages. Accessible on the Internet at URL: https://www.uniprot.org/uniprot/F6U119.
UniProt Consortium (Jul. 27, 2011) "Interleukin-1: IL37," UniProt Accession No. F7I5B4. 5 pages. Accessible on the Internet at URL: https://www.uniprot.org/uniprot/F7I5B4.
UniProt Consortium (Nov. 8, 2002) "Interleukin-37: IL37," UniProt Accession No. Q9NZH6. 13 pages. Accessible on the Internet at URL: https://www.uniprot.org/uniprot/Q9NZH6.
Ellisdon et al. (2017) "Homodimerization attenuates the anti-inflammatory activity of interleukin-37," Science Immunology. 2(1548):1-12.
Supplementary European Search Report corresponding to European Patent Application No. 16810615.1, dated Oct. 29, 2018, 10 pages.
Quirk et al. (2014) "Immunobiology of IL-37: mechanism of action and clinical perspectives," Expert Review of Clinical Immunology. 10:1703-1709.
Adams et al. (2010) "PHENIX: A Comprehensive Pythonbased System for Macromolecular Structure Solution", Acta Crystallographica Section D, D66:213-221.
Al-Obeidi et al. (1998) "Peptide and Peptidomimetic Libraries", Molecular Biotechnology, 9:205-223.
Altschul et al. (1990) "Basic Local Alignment Search Tool", Journal of Molecular Biology, 215:403-410.

(Continued)

*Primary Examiner* — Vanessa L. Ford
*Assistant Examiner* — Bruce D. Hissong
(74) *Attorney, Agent, or Firm* — Mintz Levin Cohn Ferris Glovsky and Popeo, P.C.; Ingrid A. Beattie

(57) ABSTRACT

This invention relates to polypeptides, including variants of interleukin-37 (IL-37), and related therapeutics and compositions. The invention also relates to the use of the polypeptides and compositions in methods of treating inflammatory diseases or conditions. The present invention provides a monomeric anti-inflammatory polypeptide comprising an amino acid sequence of an IL-37 monomer, the amino acid sequence having a mutation or modification for preventing the anti-inflammatory peptide from forming a homodimer.

22 Claims, 17 Drawing Sheets

Specification includes a Sequence Listing.

(56) References Cited

OTHER PUBLICATIONS

Altschul et al. (1997) "Gapped BLAST and PSI-BLAST: A New Generation of Protein Database Search Programs", Nucleic Acids Research, 25(17):3389-3402.
Barany et al. (1987) "Solid-Phase Peptide Synthesis: A Silver Anniversary Report", International Journal of Peptide and Protein Research, 30(6):705-739.
Bauer et al. (1985) "A Genetic Enrichment for Mutations Constructed by Oligodeoxynucleotide-Directed Mutagenesis", Gene, 37(1-3):73-81.
Bunkóczi et al. (2013) "Phaser.MRage: Automated Molecular Replacement", Acta Crystallographica Section D, D69:2276-2286.
Chen et al. (2010) "MolProbity: All-Atom Structure Validation for Macromolecular Crystallography", Acta Crystallographica Section D, D66:12-21.
Collaborative Computational Project (1994) "The CCP4 Suite: Programs for Protein Crystallography", Acta Crystallographica Section D, D50:760-763.
Connolly et al. (Jun. 28, 2012) "New Developments in Toll-Like Receptor Targeted Therapeutics", Current Opinion in Pharmacology, 12(4):510-518.
Craik (Jan.-Feb. 1985) "Use of Oligonucleotides for Site-specific Mutagenesis", BioTechniques, 3(1):12-17.
Database Genbank "Interleukin-37 Isoform 1 [*Homo sapiens*]", Genbank Accession No. NP_055254.2, 3 pages.
Dinarello et al. (May 2016) "Suppression of Innate Inflammation and Immunity by Interleukin-37", European Journal of Immunology, 46(5):30 pages.
Dunn et al. (Aug. 26, 2003) "High-Resolution Structure of Murine Interleukin 1 Homologue IL-1F5 Reveals Unique Loop Conformations for Receptor Binding Specificity", Biochemistry, 42(37):10938-10944.
Emsly et al. (2004) "Coot: Model-Building Tools for Molecular Graphics", Acta Crystallographica Section D, D60:2126-2132.
Hruby et al. (1997) "Synthesis of Oligopeptide and Peptidomimetic Libraries", Current Opinion in Chemical Biology, 1:114-119.
Karlin et al. (Jun. 1993) "Applications and Statistics for Multiple High-Scoring Segments in Molecular Sequences", Proceedings of the National Academy of Sciences, 90(12):5873-5787.
Karlin et al. (Mar. 1990) "Methods for Assessing the Statistical Significance of Molecular Sequence Features by Using General Scoring Schemes", PNAS, 87:2264-2268.
Kato et al. (Nov. 2003, e-published Oct. 5, 2003; "The Structure and Binding Mode of Interleukin-18", Nature Structural & Molecular Biology, 10(11):966-971.
Krissinel et al. (Sep. 21, 2007) "Inference of Macromolecular Assemblies from Crystalline State", Journal of Molecular Biology, 372(3):774-797.
Kumar et al. (Apr. 21, 2002) "Interleukin-1F7B (IL-1H4/IL-1F7) is Processed by Caspase-1 and Mature IL-1F7B Binds to the IL-18 Receptor but does not Induce IFN-Gamma Production", Cytokine, 18(2):61-71.
Luckow et al. (1988) "Trends in the Development of Baculovirus Expression Vectors", Biotechnology, 6:47-55.
Matsuura et al. (Dec. 16, 2004) "Structural Basis for the Assembly of a Nuclear Export Complex", Nature, 432 (7019):872-877.
Merrifield (Jul. 1, 1963) "Solid Phase Peptide Synthesis. I. The Synthesis of a Tetrapeptide", Journal of the American Chemical Society, 85(14):2149-2154.
Myers et al. (1988) "Optimal Alignments in Linear Space", Computer Applications in the Biosciences, 4(1):11-17.
Nold et al. (2008) "Endogenous IL-32 Controls Cytokine and HIV-1 Production", Journal of Immunology, 181 (1):557-565.
Nold et al. (2003) "IL-18bpa:Fc Cooperates with Immunosuppressive Drugs in Human Whole Blood", Biochemical Pharmacology, 66(3):505-510.
Nold et al. (Nov. 2010, e-published Oct. 10, 2010) "IL-37 is a Fundamental Inhibitor of Innate Immunity", Nature Immunology, 11:1014-1022.
Nold-Petry et al. (Apr. 2015, e-published Mar. 2, 2015) "IL-37 Requires the Receptors IL-18R$\alpha$ and IL-1R8 (SIGIRR) to Carry Out its Multifaceted Anti-Inflammatory Program Upon Innate Signal Transduction", Nature Immunology, 16(4):354-365.
Ostergaard et al. (1997) "Peptomers: A Versatile Approach for the Preparation of Diverse Combinatorial Peptidomimetic Bead Libraries", Molecular Diversity, 3:17-27.
Ostresh et al. (1996) "Generation and use of Nonsupport-Bound Peptide and Peptidomimetic Combinatorial Libraries", Methods in Enzymology, 267:220-234.
Thompson et al. (1994) "Clustal W: Improving the Sensitivity of Progressive Multiple Sequence Alignment Through Sequence Weighting, Position-Specific Gap Penalties and Weight Matrix Choice", Nucleic Acids Research, 22(22):4673-4680.
Tsutsumi et al. (Dec. 15, 2014) "The Structural Basis for Receptor Recognition of Human Interleukin-18", Nature Communications, 5:13 pages.
Walder et al. (1986) "Oligodeoxynucleotide-Directed Mutagenesis Using the Yeast Transformation System", Gene, 42(2):133-139.
Woodbury et al. (Apr. 2002) "Complex Behavior in Solution of Homodimeric SecA", Protein Science, 11(4):875-882.
Bulau et al., "Role of caspase-1 in nuclear translocation of IL-37, release of the cytokine, and IL-37 inhibition of innate immune responses", PNAS 111(7): 2650-2655 (Feb. 18, 2014).

* cited by examiner

FIG. 4

MSFVGENSGVKMGSEDWEKDEPQCCLEDPAGSPLEPGPSLPTMNFVHTSPKVKNLN
PKKFSIHDQDHKVLVLDSGNLIAVPDKNYIRPEIFFALASSLSSASAEKGSPILLGVSKGE
FCLYCDKDKGQSHPSLQLKKEKLMKLAAQKESARRPFIFYRAQVGSWNMLESAAHPG
WFICTSCNCNEPVGVTDKFENRKHIEFSFQPVCKAE MSPSEVSD (SEQ ID NO: 1)

SEQUENCE LISTING

<160> NUMBER OF SEQ ID NOS: 1

<210> SEQ ID NO 1
<211> LENGTH: 218
<212> TYPE: PRT
<213> ORGANISM: Homo sapiens

<400> SEQUENCE: 1

```
Met Ser Phe Val Gly Glu Asn Ser Gly Val Lys Met Gly Ser Glu Asp
1               5                   10                  15

Trp Glu Lys Asp Glu Pro Gln Cys Cys Leu Glu Asp Pro Ala Gly Ser
            20                  25                  30

Pro Leu Glu Pro Gly Pro Ser Leu Pro Thr Met Asn Phe Val His Thr
        35                  40                  45

Ser Pro Lys Val Lys Asn Leu Asn Pro Lys Lys Phe Ser Ile His Asp
    50                  55                  60

Gln Asp His Lys Val Leu Val Leu Asp Ser Gly Asn Leu Ile Ala Val
65                  70                  75                  80

Pro Asp Lys Asn Tyr Ile Arg Pro Glu Ile Phe Phe Ala Leu Ala Ser
            85                  90                  95

Ser Leu Ser Ser Ala Ser Ala Glu Lys Gly Ser Pro Ile Leu Leu Gly
            100                 105                 110

Val Ser Lys Gly Glu Phe Cys Leu Tyr Cys Asp Lys Asp Lys Gly Gln
            115                 120                 125

Ser His Pro Ser Leu Gln Leu Lys Lys Glu Lys Leu Met Lys Leu Ala
    130                 135                 140

Ala Gln Lys Glu Ser Ala Arg Arg Pro Phe Ile Phe Tyr Arg Ala Gln
145                 150                 155                 160

Val Gly Ser Trp Asn Met Leu Glu Ser Ala Ala His Pro Gly Trp Phe
                165                 170                 175

Ile Cys Thr Ser Cys Asn Cys Asn Glu Pro Val Gly Val Thr Asp Lys
            180                 185                 190

Phe Glu Asn Arg Lys His Ile Glu Phe Ser Phe Gln Pro Val Cys Lys
        195                 200                 205

Ala Glu Met Ser Pro Ser Glu Val Ser Asp
210                 215
```

IL-37 VARIANTS

CROSS REFERENCE(S) TO RELATED APPLICATIONS

This application is a national stage application filed under 35 U.S.C. § 371, of International Patent Application No. PCT/AU2016/050495, filed Jun. 15, 2016, which claims priority from Australian provisional applications 2015902262, filed Jun. 15, 2015 and 2016900703, filed Feb. 26, 2016 the entire contents of each of which are incorporated herein by reference.

INCORPORATION BY REFERENCE OF SEQUENCE LISTING

The contents of the text file named "028616-504N01US_ST25.TXT", which was created on Dec. 15, 2017 and is 2.17 KB in size, are hereby incorporated by reference in their entireties and for all purposes.

FIELD OF THE INVENTION

This invention relates to polypeptides, including variants of interleukin-37 (IL-37), and related therapeutics and compositions. The invention also relates to the use of the polypeptides and compositions in methods of treating inflammatory diseases or conditions.

BACKGROUND OF THE INVENTION

Inflammation plays a fundamental role in host defenses and the progression of immune-mediated diseases. The inflammatory response is initiated in response to tissue injury (e.g., trauma, ischemia, and foreign particles) and infection by a complex cascade of events, including chemical mediators (e.g., cytokines and prostaglandins) and inflammatory cells (e.g., leukocytes). The inflammatory response is characterized by increased blood flow, increased capillary permeability, and the influx of phagocytic cells. These events result in swelling, redness, warmth (altered heat patterns), and pus formation at the site of injury.

An interplay between the humoral and cellular immune elements in the inflammatory response enables the elimination of harmful agents and the initiation of the repair of damaged tissue. When this interplay is disrupted, the inflammatory response may result in considerable damage to normal tissue of uncontrolled inflammatory responses, clinical intervention is needed to prevent tissue damage and organ dysfunction.

Interleukin-37 (IL-37) is a member of the IL-1 family of cytokines with unique and broad anti-inflammatory effects in innate and adaptive immunity. IL-37 specifically decreases inflammation mediated by pro-inflammatory cytokines such as IL-1β and TNF via their receptors, as well as Toll-Like Receptor ligands and has extensive protective roles in inflammation triggered by infection or other non-infectious assaults. IL-37 initiates signaling both at the cell membrane, through interaction with IL-18 receptor a and IL-1R8 (Sigirr), and within the cell through interactions with Smad3. However, an understanding of the relationship between structure, function and regulation of IL-37 activity is currently lacking.

There exists a need for improved anti-inflammatory compositions and methods of treatment.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides a monomeric anti-inflammatory polypeptide comprising an amino acid sequence of an IL-37 monomer, the amino acid sequence having a mutation or modification for preventing the anti-inflammatory peptide from forming a homodimer.

The present invention provides an anti-inflammatory polypeptide comprising an amino acid sequence of an IL-37 polypeptide, the amino acid sequence having a mutation or modification that reduces the capacity of the anti-inflammatory polypeptide to form a dimer.

Preferably, the mutation or modification reduces or prevents the polypeptide from forming a dimerization interface that enables dimerization of IL-37 monomers. Typically, the mutation or modification is located in a region of the peptide that has the same amino acid sequence as the amino acid sequence that forms the dimerization interface of an IL-37 monomer. Mutation or modification may be located in the β3 or β4 loops that form the dimerization interface of an IL-37 monomer.

The present invention provides a polypeptide comprising an amino acid sequence of an IL-37 polypeptide or fragment thereof, wherein the polypeptide has a reduced capacity to form a dimer compared to a polypeptide having the sequence of SEQ ID NO: 1.

The present invention provides a polypeptide comprising an amino acid sequence having at least 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1, wherein the polypeptide has a reduced capacity to form a dimer compared to a polypeptide having the sequence of SEQ ID NO: 1.

The present invention provides an IL-37 polypeptide that has a reduced capacity to form a dimer compared to a polypeptide having the sequence of SEQ ID NO: 1.

The present invention provides a polypeptide comprising an amino acid sequence of an IL-37 polypeptide or fragment thereof, wherein the polypeptide has a reduced capacity to form a dimer compared to a polypeptide having the sequence of SEQ ID NO: 1, wherein the polypeptide has a mutation or modification of at least one residue located in a position equivalent to the β3-β4 loop region in SEQ ID NO: 1. Preferably, the β3-β4 loop region consists of, or is equivalent to, residues 83 to 91 of SEQ ID NO: 1. Preferably, the mutation or modification occurs for a residue at a position, or at a position equivalent to, K83, N84, Y85, I86, R87 and/or P88. Preferably, the mutation is a replacement with a non-conservative residue, more preferably, the mutation is replacement with alanine or an amino acid with an opposite charge.

The present invention provides a polypeptide comprising an amino acid sequence of an IL-37 polypeptide or fragment thereof, wherein the polypeptide has a reduced capacity to form a dimer compared to a polypeptide having the sequence of SEQ ID NO: 1, wherein the polypeptide has a mutation or modification of a residue at, or at a position equivalent to, D73, K83 and Y85. Preferably, the mutation is a replacement with a non-conservative amino acid residue, more preferably, the mutation is replacement with alanine or an amino acid with an opposite charge. More preferably, the mutation is any one or more of D73A, D73K, K83E, K83A and Y85A.

The present invention provides a polypeptide comprising an amino acid sequence of an IL-37 polypeptide or fragment thereof, wherein the polypeptide has a reduced capacity to form a dimer compared to a polypeptide having the sequence of SEQ ID NO: 1, wherein the polypeptide has a mutation or modification of, or at a position equivalent to, V71, V80 and I78. Preferably, the mutation is a replacement with a non-conservative residue, more preferably, the mutation is replacement with alanine or an amino acid with an opposite charge.

The present invention provides an IL-37 polypeptide that has a reduced capacity to form a dimer compared to a polypeptide having the sequence of SEQ ID NO: 1, wherein the polypeptide has modification of the region equivalent to the β3-β4 loop region in SEQ ID NO: 1. Modification includes, deleting the loop, shortening the loop, lengthening the loop, mutating residues of the loop and/or chemically modifying loop residues.

The present invention provides a monomeric polypeptide comprising an amino acid sequence having at least 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1.

The present invention provides an isolated, recombinant or synthetic IL-37 polypeptide that exists as a monomer.

The present invention provides a polypeptide that comprises a paralogous or an orthologous sequence to the sequence shown in SEQ ID NO: 1, wherein the polypeptide exist as a monomer or has a reduced capacity to form a dimer compared to a polypeptide having the sequence of SEQ ID NO: 1. Preferably, the polypeptide that comprises a paralogous or orthologous sequences to the sequence shown in SEQ ID NO: 1 has a mutation or modification in a residue that is located in a dimerization interface that is equivalent to the dimerization interface as described herein for SEQ ID NO: 1, for example the residues in Table 1.

A polypeptide of the invention may be isolated, purified, substantially purified, enriched, synthetic or recombinant.

As used herein, the reduced capacity to form a dimer may refer to a reduced capacity to form a heterodimer and/or homodimer.

The invention also provides a polypeptide that comprises, consists essentially of or consists of an amino acid sequence of a IL-37 polypeptide or fragment thereof, wherein the amino acid sequence contains at least one mutation of, or modification to, a residue at, or at a position equivalent to, the dimer interface of SEQ ID NO: 1. The dimer interface in relation to a polypeptide having an amino acid sequence of SEQ ID NO: 1 includes the residues in Table 1. Typically, the polypeptide comprises an amino acid sequence that contains a mutation or modification of a residue at, or at a position equivalent to, 73, 83 and 85 of SEQ ID NO: 1. More preferably, the mutation is any one or more of D73A, D73K, K83E, K83A and Y85A.

The present invention provides an isolated, recombinant or synthetic IL-37 polypeptide that does not have the capacity to form a dimer or has a reduced capacity to form a dimer. In this or any other aspect of the invention described herein, the capacity of a polypeptide to form a dimer may be determined by any method described herein, including size exclusion chromatography and multi-angle light scattering, analytical gel electrophoresis under non-denaturing conditions, analytical centrifugation, mass spectrometry or reverse phase high performance liquid chromatography (RP-HPLC).

Reduction in dimer formation can be compared to a reference polypeptide. The reference polypeptide will typically be a native, wildtype, unmodified or unmutated IL-37 polypeptide. Preferably, the reference polypeptide has an amino acid sequence of SEQ ID NO: 1. Alternatively, if the polypeptide of the invention has an amino acid sequence that is paralogous or orthologous to SEQ ID NO: 1, then the reference peptide is the native, wildtype, unmodified or unmutated paralogous or orthologous amino acid sequence.

The present invention provides a polypeptide comprising an amino acid sequence having at least 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1, wherein the amino acid residue at, or equivalent to:

position 71 in SEQ ID NO: 1 is not a Val;
position 72 in SEQ ID NO: 1 is not an Leu;
position 73 in SEQ ID NO: 1 is not a Asp;
position 74 in SEQ ID NO: 1 is not a Ser;
position 78 in SEQ ID NO: 1 is not an Ile;
position 80 in SEQ ID NO: 1 is not a Val;
position 83 in SEQ ID NO: 1 is not a Lys;
position 84 in SEQ ID NO: 1 is not an Asn;
position 85 in SEQ ID NO: 1 is not a Tyr;
position 86 in SEQ ID NO: 1 is not an Ile;
position 87 in SEQ ID NO: 1 is not an Arg;
position 88 in SEQ ID NO: 1 is not a Pro; and/or
position 184 in SEQ ID NO: 1 is not an Asn. Preferably, the amino acid residue is a non-conservative substitution relative to the amino acid that occurs in that position in SEQ ID NO: 1. In one embodiment, the amino acid at position 85 is an alanine, the amino acid at position 83 is a glutamate, the amino acid at position 73 is an alanine and/or the amino acid at position 73 is a lysine. In one embodiment, the amino acid residue at, or at a position equivalent to, position 71, 72, 73, 74, 78, 80, 83, 84, 85, 86, 87, 88 and/or 184 in SEQ ID NO: 1 is deleted.

In relation to any polypeptide of the invention described herein, the polypeptide may have an N-terminal truncation of, or of residues equivalent to, 1 to 20 or 1 to 45 of SEQ ID NO: 1.

Any polypeptide of the invention described herein may also exhibit greater anti-inflammatory properties compared to a polypeptide having an amino acid sequence of SEQ ID NO: 1, an IL-37 amino acid sequence that is unmodified or unmutated, or a IL-37 polypeptide that does not exhibit a reduced capacity to form a dimer. The anti-inflammatory properties may be determined by an assay described herein, particularly in the Examples, including Examples 1, 3 and 4. In one embodiment, a polypeptide of the invention exhibits anti-inflammatory properties at concentrations less than or about 1 ug/ml, 100 ng/ml, 10 ng/ml, 100 pg/ml, 10 pg/ml or 1 pg/ml when tested in an assay as described herein including the LPS-stimulated IL-1β assay described in Example 1 and 3. Inflammatory insults may include ligands of a Toll-like receptor (TLR) 2, 4, 7, 8 and/or 9, such as HKLM, imiquimod, CpG-A or ssRNA40. A polypeptide of the invention may reduce IL-1β by at least 30% at 10 pg/ml, at least 40% at 10 ng/ml or at least about 50% at any one or more of 1 pg/ml, 10 pg/ml, 100 pg/ml, 10 ng/ml or 100 ng/ml when tested in the LPS-stimulated IL-1β assay described in Example 1 and 3. Reduction in other proinflammatory cytokines such as IL-6 may also be observed. A polypeptide of the invention may exhibit no statistically significant difference in anti-inflammatory property when tested at 10 ng/ml and 100 ng/ml in an assay described herein including the LPS-stimulated IL-1β assay described in Example 1 and 3. A polypeptide of the invention may exhibit an anti-inflammatory property identical or similar to a mutated IL-37 described in the Examples.

The invention provides a pharmaceutical composition for treating or preventing an inflammatory disease or condition comprising a polypeptide of the invention and a pharmaceutically acceptable diluent, excipient or carrier. In one embodiment, the only active ingredient present in the composition is a polypeptide of the invention.

The invention provides a pharmaceutical composition for treating or preventing an inflammatory disease or condition comprising as an active ingredient a polypeptide of the invention and a pharmaceutically acceptable diluent, excipient or carrier. In one embodiment, the only active ingredient present in the composition is a polypeptide of the invention.

The invention provides a pharmaceutical composition for treating or preventing an inflammatory disease or condition comprising as a main ingredient a polypeptide of the invention and a pharmaceutically acceptable diluent, excipient or carrier. In one embodiment, the only active ingredient present in the composition is a polypeptide of the invention.

The invention also provides a polypeptide of the invention for use in the treatment of an inflammatory disease or condition.

The invention also provides a pharmaceutical composition comprising a polypeptide of the invention and a pharmaceutically acceptable diluent, excipient or carrier for use in the treatment of an inflammatory disease or condition.

The invention also provides a method of inhibiting inflammation in a subject in need thereof, the method comprising administering to the subject a therapeutically effective amount of a polypeptide of the invention, or a pharmaceutical composition of the invention, thereby inhibiting inflammation.

The present invention provides a method for the treatment or prevention of an inflammatory disease or condition, the method comprising the step of administering a composition to the subject for treatment or prevention, wherein the composition comprises, consists essentially of or consists of polypeptide of the invention and a pharmaceutically acceptable diluent, excipient or carrier.

In any method or use of the invention described herein, a polypeptide of the invention may be administered systemically or directly to the site of disease. A polypeptide of the invention may be formulated for oral administration.

The present invention provides a method of treating or preventing an inflammatory disease or condition in a subject in need thereof, the method comprising administering to the subject a therapeutically effective amount a polypeptide or pharmaceutical composition of the invention, thereby treating or preventing an inflammatory disease or condition in a subject.

The invention also provides a method of alleviating or ameliorating a symptom of an inflammatory disease or condition in a subject in need thereof, the method comprising administering to the subject in need thereof a therapeutically effective amount of a polypeptide or pharmaceutical composition of the invention, thereby alleviating or ameliorating a symptom of an inflammatory disease or condition in the subject.

The invention also provides use of a therapeutically effective amount of a polypeptide or pharmaceutical composition of the invention in the manufacture of a medicament for the treatment or prevention of an inflammatory disease or condition in a subject in need thereof.

The present invention provides a method for the treatment of an inflammatory disease or condition in a subject comprising the steps of
identifying a subject having an inflammatory disease or condition; and
administering to the subject in need thereof a therapeutically effective amount of a polypeptide or pharmaceutical composition of the invention,
thereby treating an inflammatory disease or condition in the subject.

The present invention a method for the treatment of an inflammatory disease or condition comprising the steps of
identifying a subject having an inflammatory disease or condition; and
administering to the subject in need thereof a therapeutically effective amount of a polypeptide or pharmaceutical composition of the invention,
thereby treating an inflammatory disease or condition in the subject.

The invention also provides a nucleic acid molecule encoding an a polypeptide as described herein.

The invention also provides a vector comprising a nucleic acid molecule described herein.

The invention also provides a cell comprising a vector or nucleic acid molecule described herein.

The invention also provides an animal or tissue derived therefrom comprising a cell described herein.

As used herein, except where the context requires otherwise, the term "comprise" and variations of the term, such as "comprising", "comprises" and "comprised", are not intended to exclude further additives, components, integers or steps. The term "including" is also used interchangeably with "comprising" and is also not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

(FIG. 1A) SDS-PAGE of purified wild-type IL-37 (1-218), and N-terminal truncated variants IL-37 (21-218) and IL-37 (46-218). A small proportion of SDS-stable IL-37 dimer is indicated. (FIG. 1B) SEC-MALS analysis of the IL-37 homodimer relative to monomeric IL-18. The SEC trace corresponds to the left y-axis and MALS determination of the averaged molecular weight (right y-axis) displayed as a dashed line below the refractive index trace. (FIG. 1C) Overview of the IL-37 homodimer viewed from two orientations, related by a 90° clockwise about the horizontal axis. The structure is displayed in cartoon format with IL-37A on the left and IL-37B on the right (FIGS. 1A and 1B used to differentiate the IL-37 molecules in the homodimer).

(FIG. 2A) The IL-37 homodimer in cartoon format with the $C_2$ symmetry axis of the homodimer marked with a circle. (FIG. 2B) Homodimerization interface with side chains that make critical interactions shown as sticks and hydrogen bonds as dashed lines. (FIG. 2C) The IL-37 interface rotated 180° about the horizontal compared to (FIG. 2B) with critical side chains as sticks. (FIG. 2D)

SEC-MALS analysis of IL-37 dimer interface mutants with the SEC trace corresponding to the left y-axis and MALS determination of the averaged molecular weight (right y-axis) displayed as a dashed line below the refractive index trace.

Figure 3:
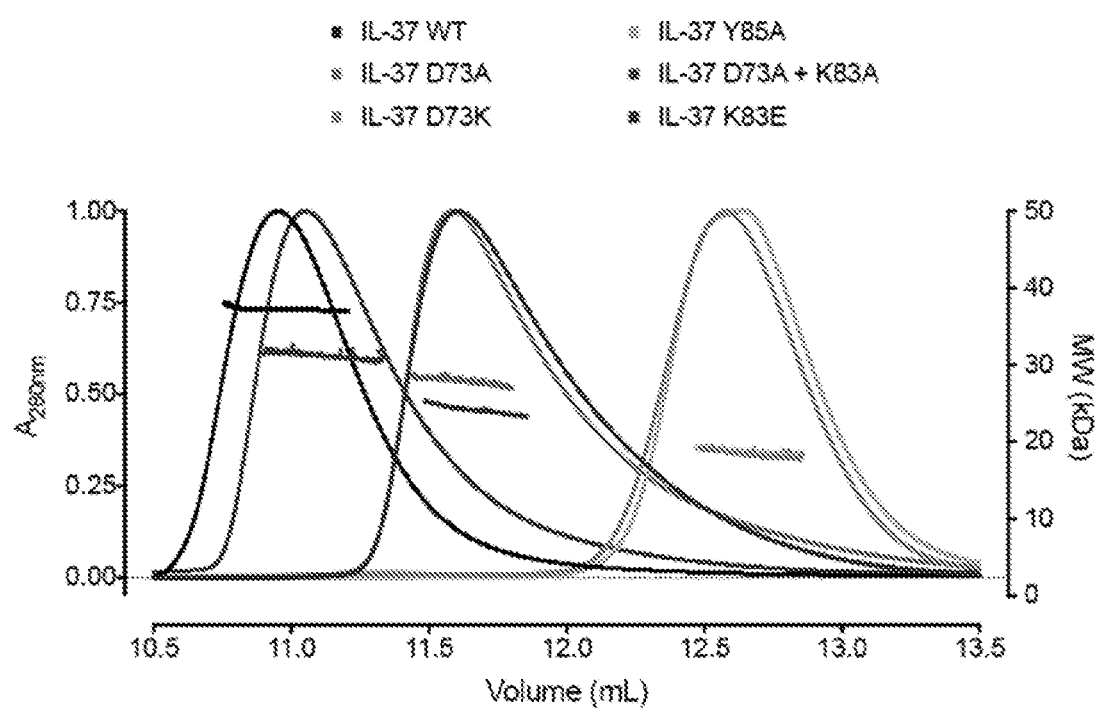

FIG. 3: SEC MALS of IL-37 dimer interface. SEC-MALS analysis of wild-type IL-37 and IL-37 interface mutants. SEC monitored by absorbance at 280 nm (left axis) and the average molecular weight derived from MALS indicated on the right axis. *It should be noted that peaks situated between the dimer and wild-type peaks are characteristic of a dimer undergoing dissociation as it passes through the column (see Woodbury et al., Protein Science 2002). i.e. the protein is not at equilibrium between monomer and dimer during the SEC run but is constantly dissociating as the concentration drops upon dilution on the column.

FIG. 4: IL-37 isoform 1 (SEQ ID NO: 1). Accession number NP_055254. This is the full-length sequence of the IL-37 isoform used herein and correlate to the numbering referred to herein. The sequence used in crystal trials was from residues 46-218 of this sequence.

Figure 5:
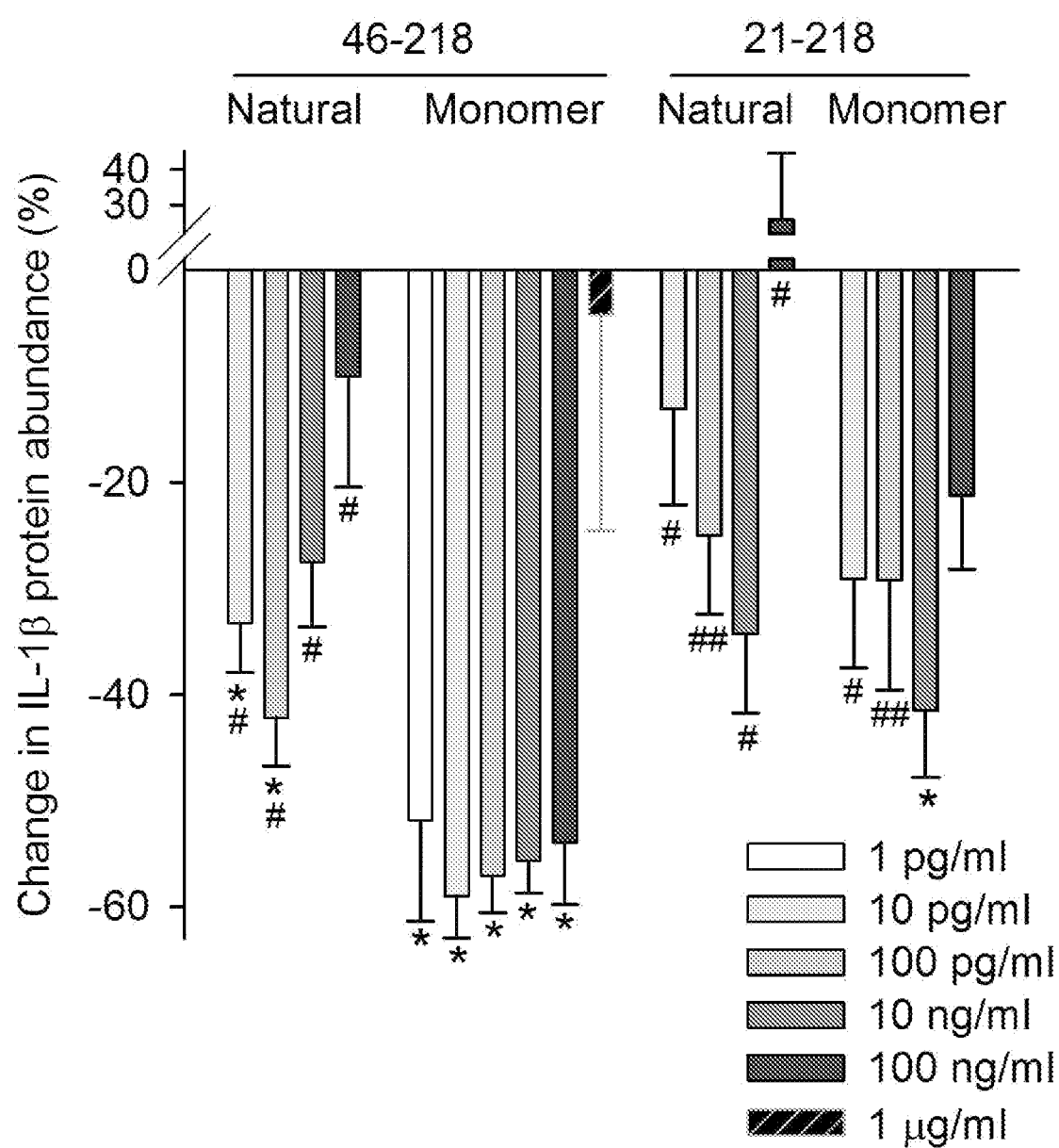

FIG. 5: Differential inhibition of LPS-stimulated IL-1β by variants of recombinant IL-37 in human PBMC. PBMC freshly isolated from healthy volunteers were incubated with the indicated concentrations of four variants of recombinant IL-37b, including the natural protein (wild-type) and the monomer-mutant (D73K), both N-terminally truncated either at amino acid 21 (21-218) or 46 (46-218). Thirty minutes thereafter, cultures were stimulated with LPS (50 pg/ml) or vehicle (no IL-1β induction, not shown). Supernatants were collected 20 h after addition of LPS and IL-1β was measured by ELISA. Graph shows IL-1β percent-change±SEM afforded by IL-37b variants compared to LPS+vehicle (set as 0); n=15 donors; *, $P<0.05$ for vehicle+ LPS vs all other groups; #, $P<0.05$ and ##, $P<0.01$ for monoIL-37 vs all other variants at the same concentration.

Figure 6:
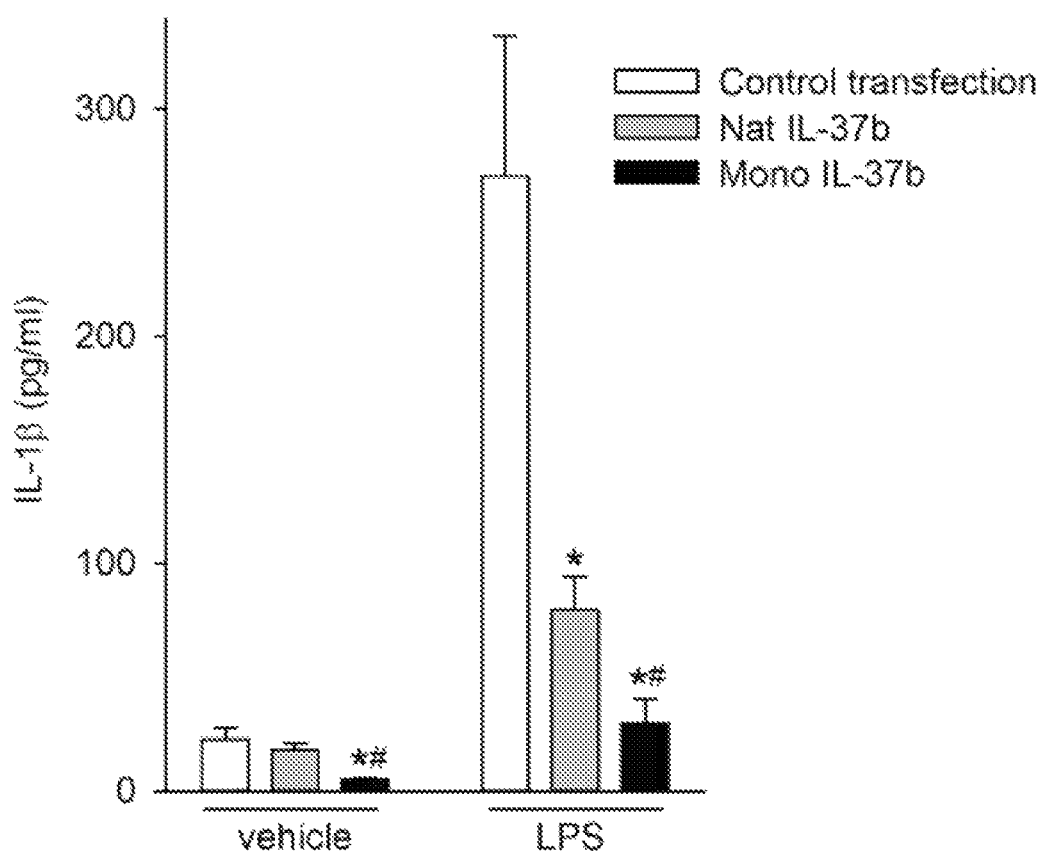

FIG. 6: Reduction of IL-1β by IL-37b variants transfected into THP-1 macrophages. THP-1 macrophages were transfected with the indicated variants of IL-37b (full length, 1-218) followed by differentiation of the cells with PMA and subsequent stimulation with LPS (250 ng/ml) or vehicle. Supernatants were collected 24 h later and assayed for IL-1β by ELISA. Supernatant IL-1β±SEM; n=11-26; *, $P<0.05$ for Control vs IL-37b transfection; #, $P<0.05$ for natIL-37b vs monoIL-37. $P<0.001$ for transfection of IL-37b variants compared to control transfection.

Figure 7:
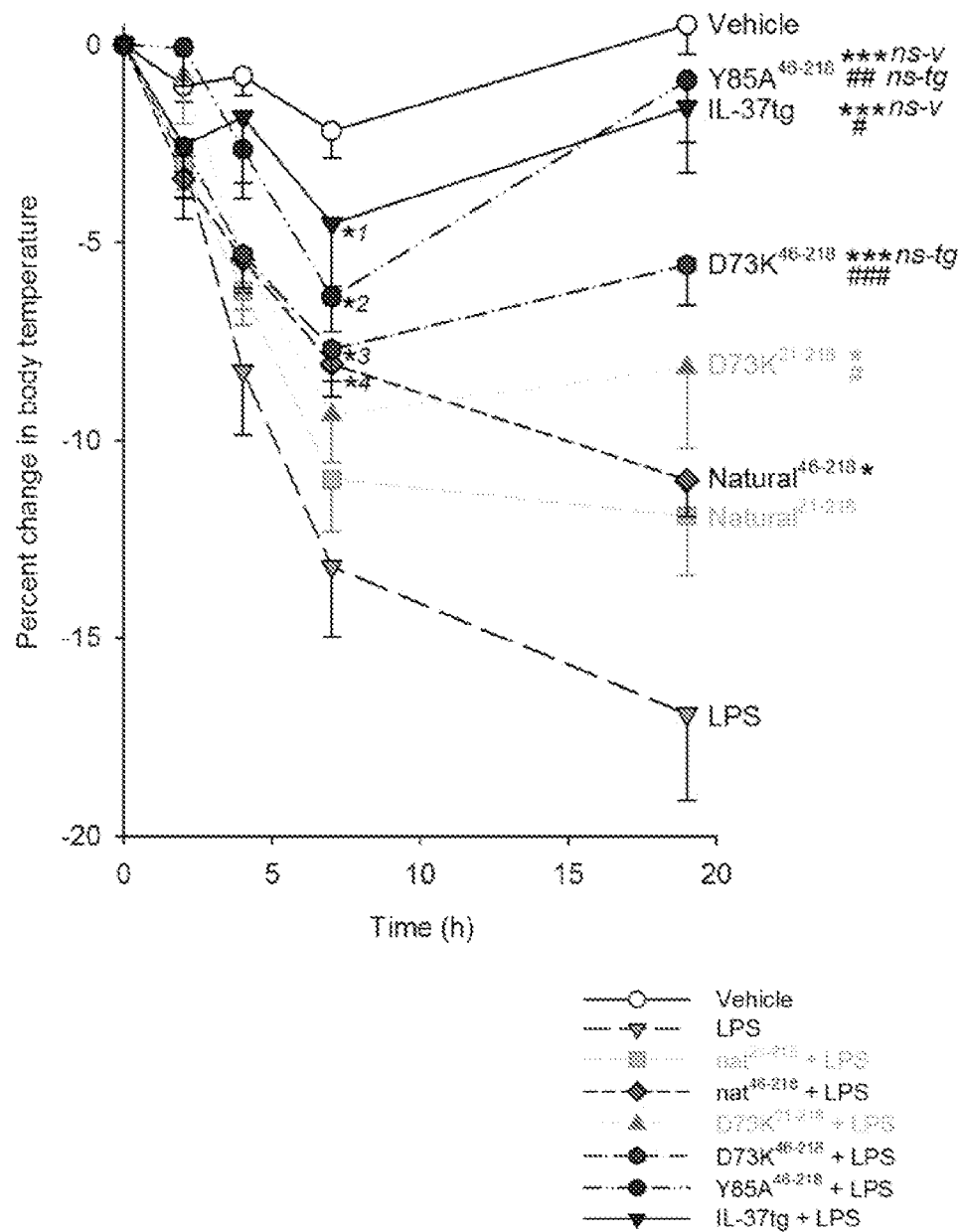

FIG. 7: C57Bl/6 wild-type (WT) mice were injected with recombinant IL-37 variants (40 μg/kg) or vehicle intraperitoneally 60 min before 10 mg/kg LPS or vehicle (time 0h). IL-37tg mice were also injected with LPS or vehicle for direct comparison. n=94 mice overall, 4-24 per group for WT, 5 for IL-37tg. Body temperature was measured at the indicated time points and is graphed±SEM; all vehicle mice are shown together. *, $P<0.05$ and ***, $P<0.001$ for LPS vs all other conditions; #, $P<0.05$, ##, $P<0.01$, and ###, $P<0.001$ for D73K or Y85A variants vs natural recIL-37; ns-tg, not significant vs IL-37tg; ns-v, not significant vs vehicle; *1-4, statistics at 7 h: *1, * and ns-v; *2, * and ns-v and ns-tg; and *3, *** and ns-tg; *4, * and ns-tg. RecIL-$37^{21-218}$ shown in grey for direct comparison, statistics for these groups were calculated separately.

Figure 8:
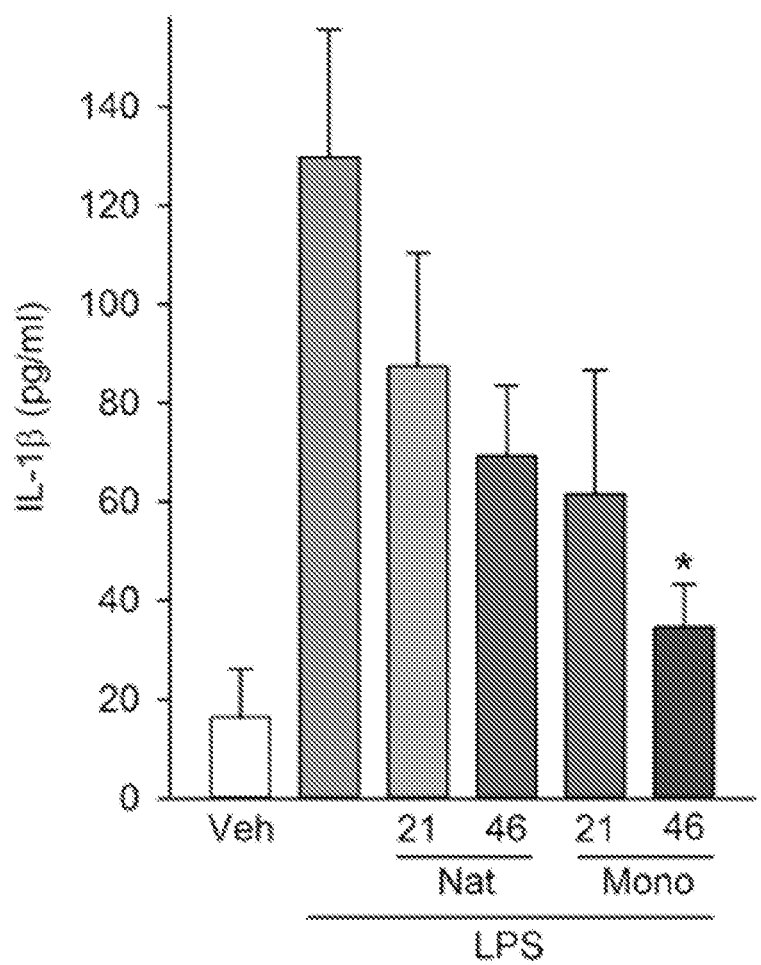

FIG. 8: As per FIG. 7, Plasma IL-1β±SEM in WT mice at 19h. Veh, vehicle; Nat, natural recIL-37; Mono, D73K; numbers indicate N-terminal truncation of the variants.

Figure 9:
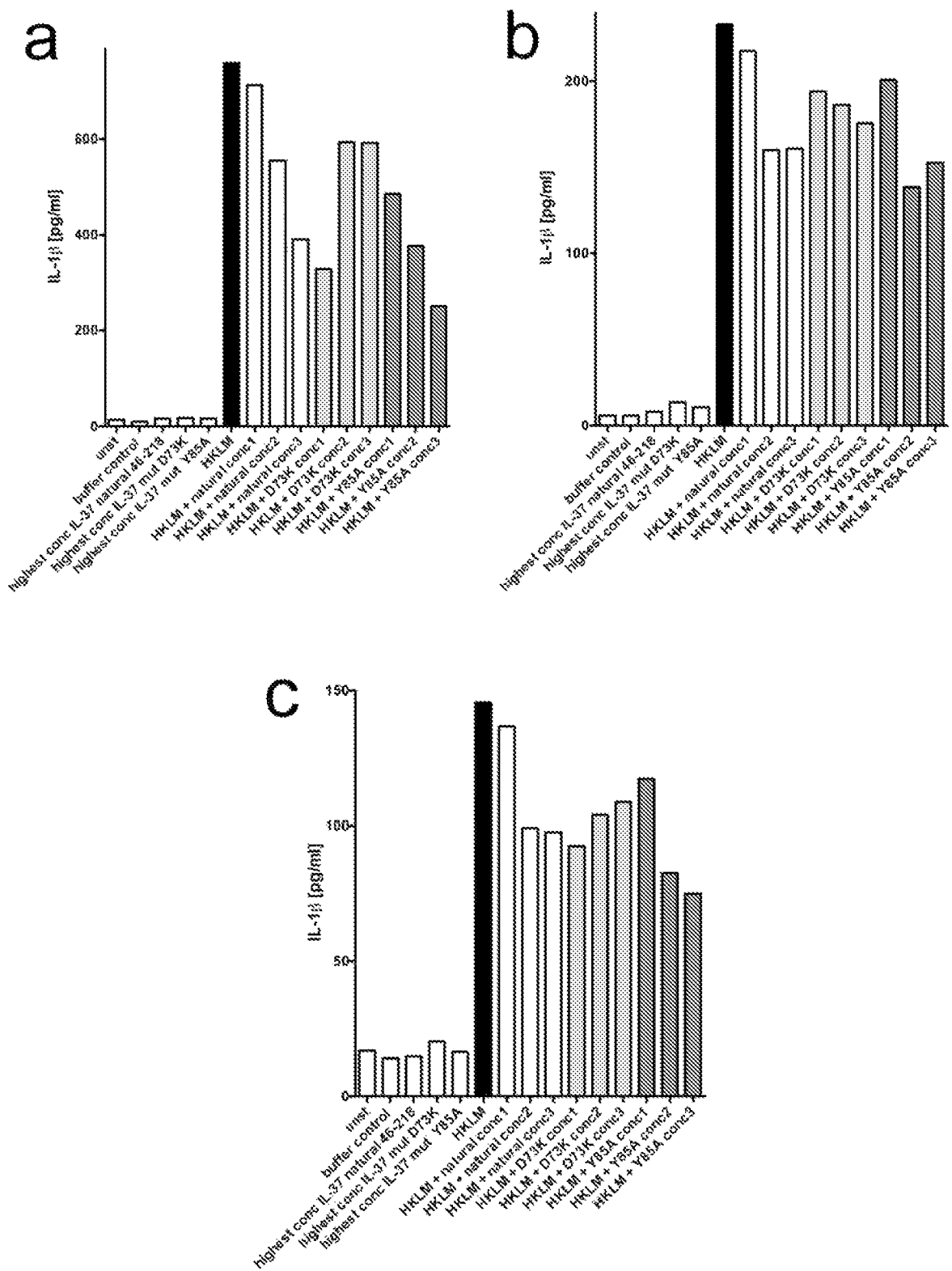
Figure 9:
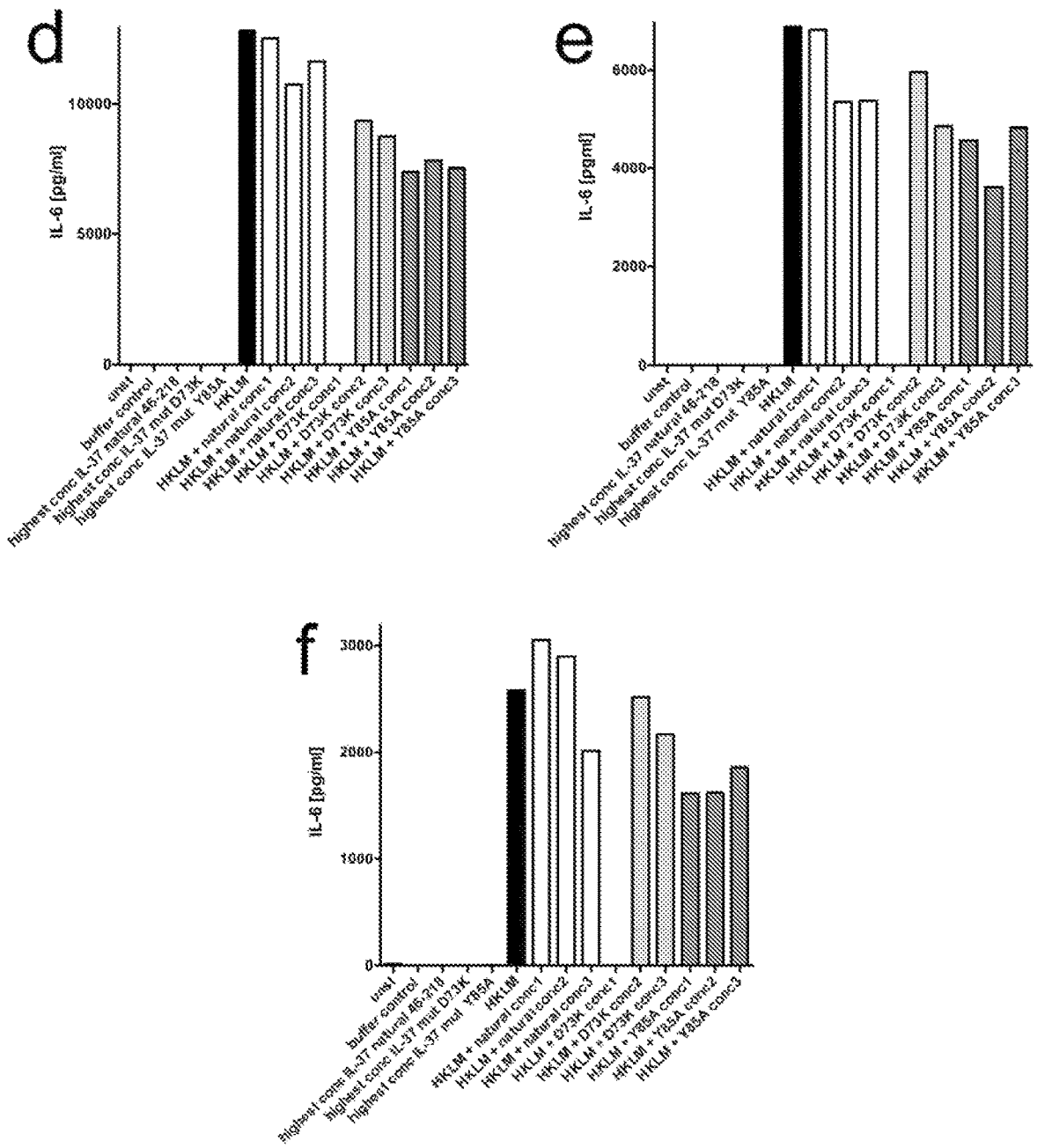
Figure 9:
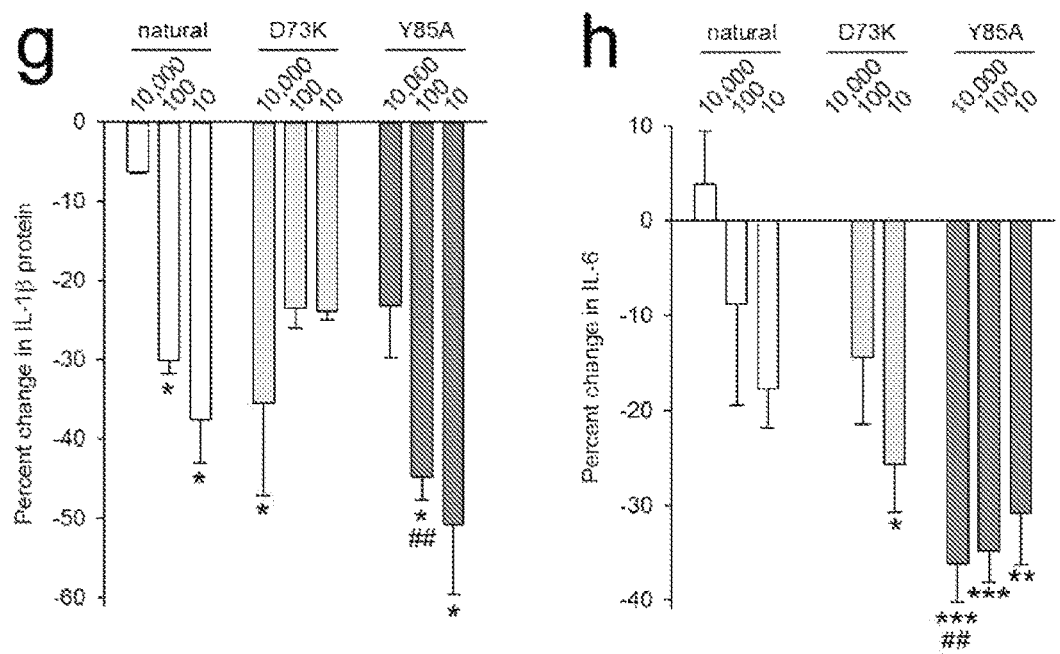

FIG. 9: Differential inhibition of HKLM-stimulated IL-1β or IL-6 by variants of recombinant IL-37 in human PBMC. Freshly isolated PBMC were stimulated as indicated. HKLM (heat-killed *Listeria monocytogenes*) was used at $10^6$ cells per ml and added 30 min after the recIL-37 variants. Black, HKLM alone; white, HKLM+ natural recIL-37; light grey, HKLM+D73K; dark grey, HKLM+ Y85A (all variants 46-218). Supernatants were collected 20 h after the addition of HKLM and IL-1β (a-c, g) and IL-6 (d-f, h) were measured by ELISA. (a-f) Concentration (conc) 1, 10 ng/ml; conc 2, 100 pg/ml; conc 3, 10 pg/ml. Graphs show absolute cytokine concentrations±SEM in the supernatants of the cultures of individual donors FC (a, d), JM (b, e), and LM (c, f). (e-f) Data for HKLM+D73K conc 1 not available. (g, h) Percent change in IL-1β (g) and IL-6 (h) was calculated from the raw data shown in panels a-f and is depicted±SEM. Concentrations of recIL-37 are indicated in pg/ml. *, $P<0.05$; , $P<0.01$; *, $P<0.001$ for HKLM alone vs HKLM+ recIL-37; ##, $P<0.01$ for Y85A vs natural recIL-37 at the same concentration.

Figure 10:
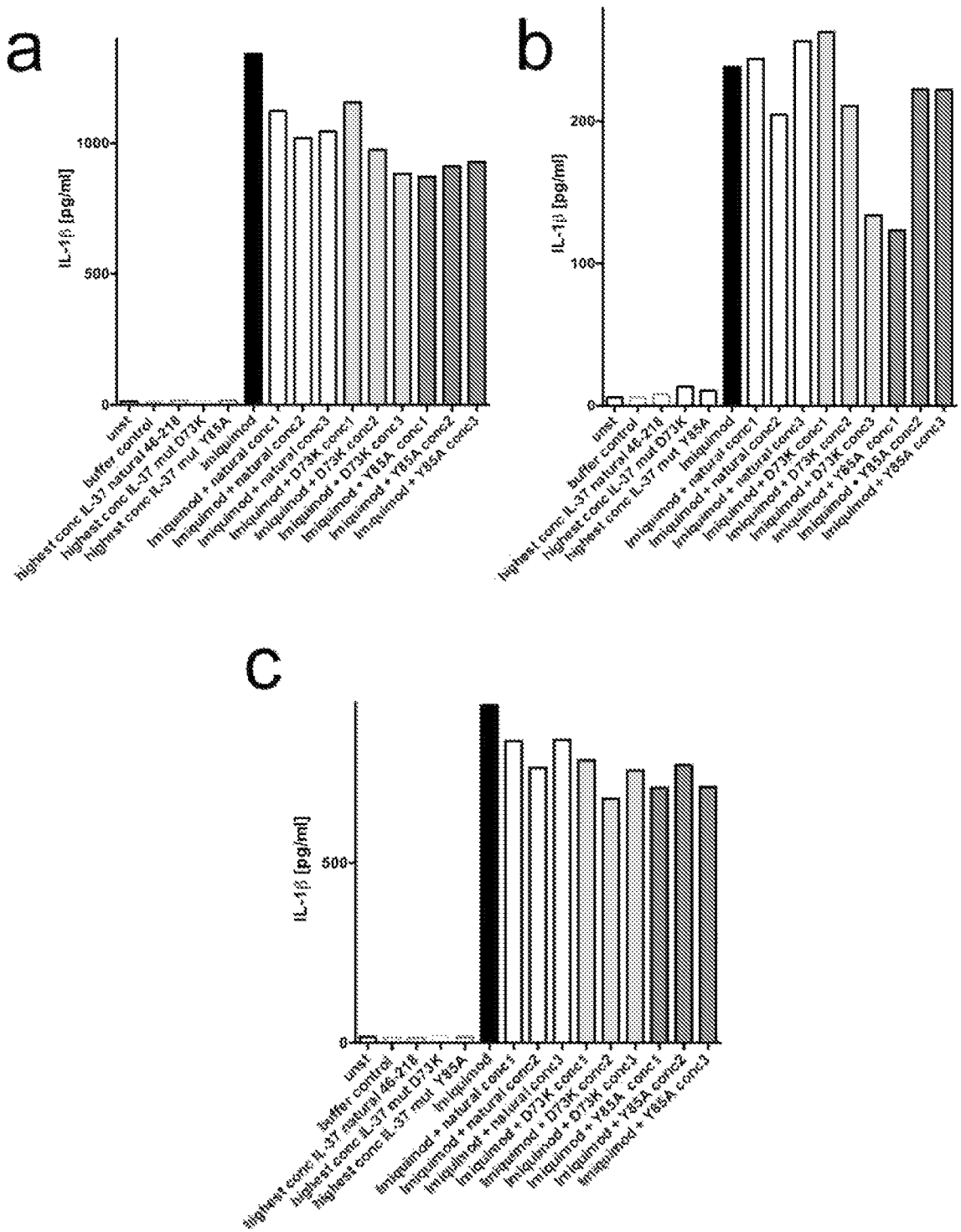
Figure 10:
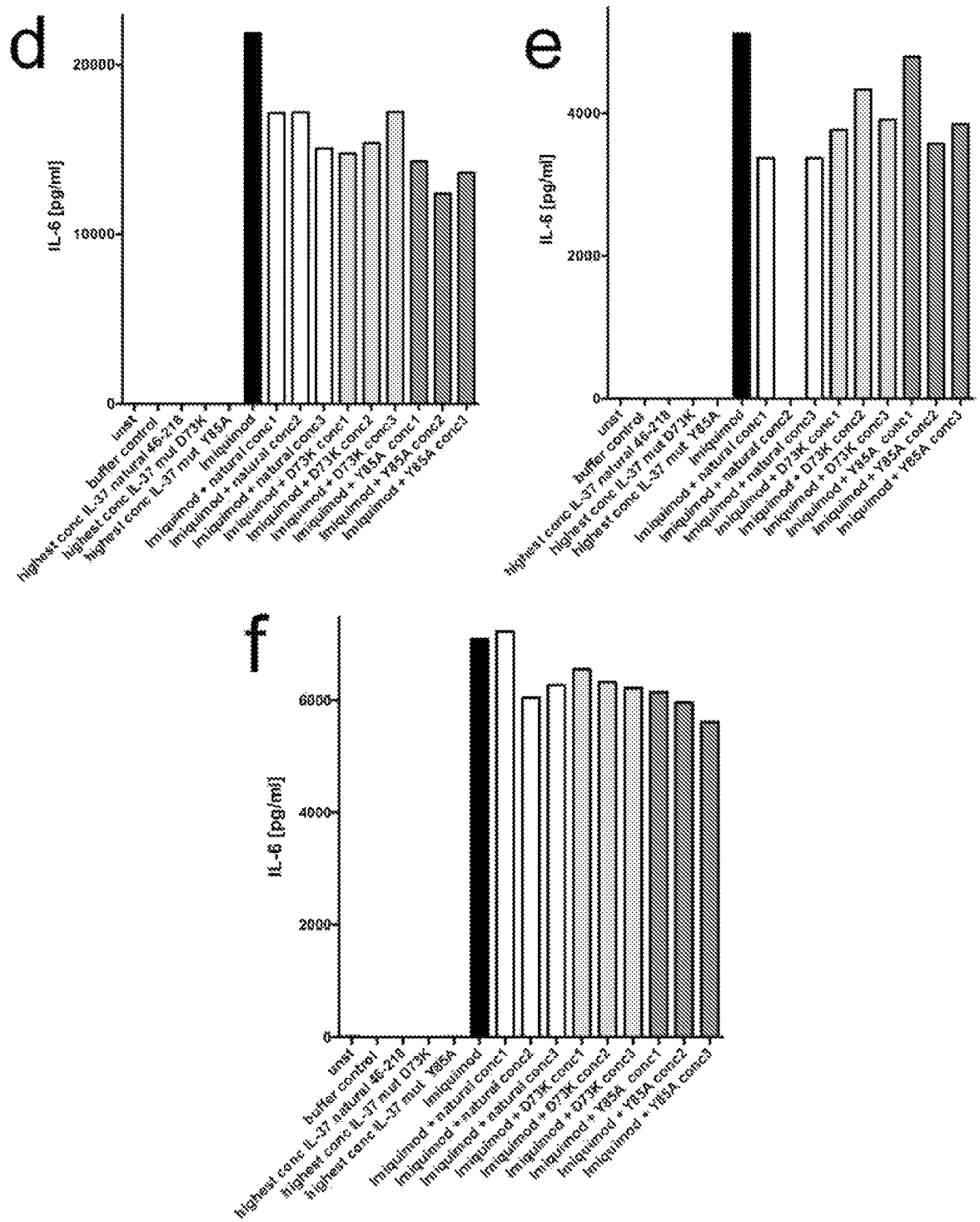
Figure 10:
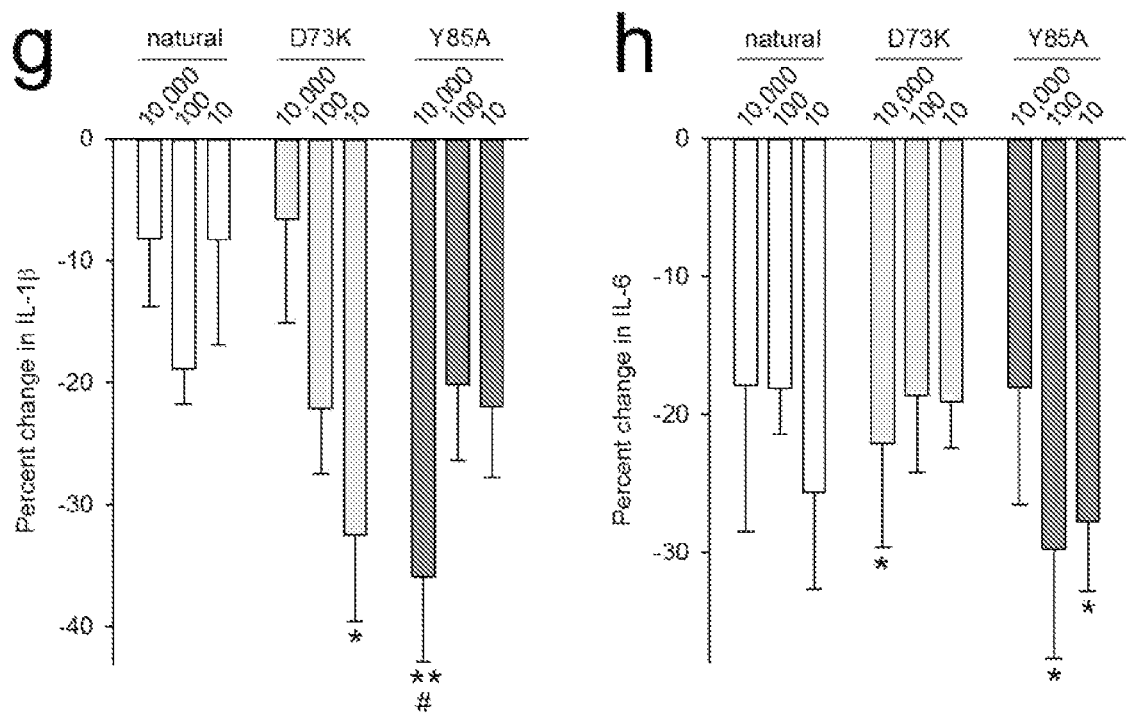

FIG. 10: Differential inhibition of imiquimod-stimulated IL-1β or IL-6 by variants of recombinant IL-37 in human PBMC. Freshly isolated PBMC were stimulated as indicated. Imiquimod was used at 10 pg/ml and added 30 min after the recIL-37b variants. Black, imiquimod alone; white, imiquimod+ natural recIL-37; light grey, imiquimod+D73K; dark grey, imiquimod+Y85A (all variants 46-218). Supernatants were collected 20 h after the addition of imiquimod and IL-1β (a-c, g) and IL-6 (d-f, h) were measured by ELISA. (a-f) Concentration (conc) 1, 10 ng/ml; conc 2, 100 pg/ml; conc 3, 10 pg/ml. Graphs show absolute cytokine concentrations±SEM in the supernatants of the cultures of individual donors FC (a, d), JM (b, e), and LM (c, f). (e) Data for imiquimod+ natural conc 2 not available. (g, h) Percent change in IL-1β (g) and IL-6 (h) was calculated from the raw data shown in panels a-f and is depicted±SEM. Concentrations of recIL-37 are indicated in pg/ml. *, $P<0.05$; **, $P<0.01$ for imiquimod alone vs imiquimod+ recIL-37; #, $P<0.05$ for Y85A vs natural recIL-37 at the same concentration.

Figure 11:
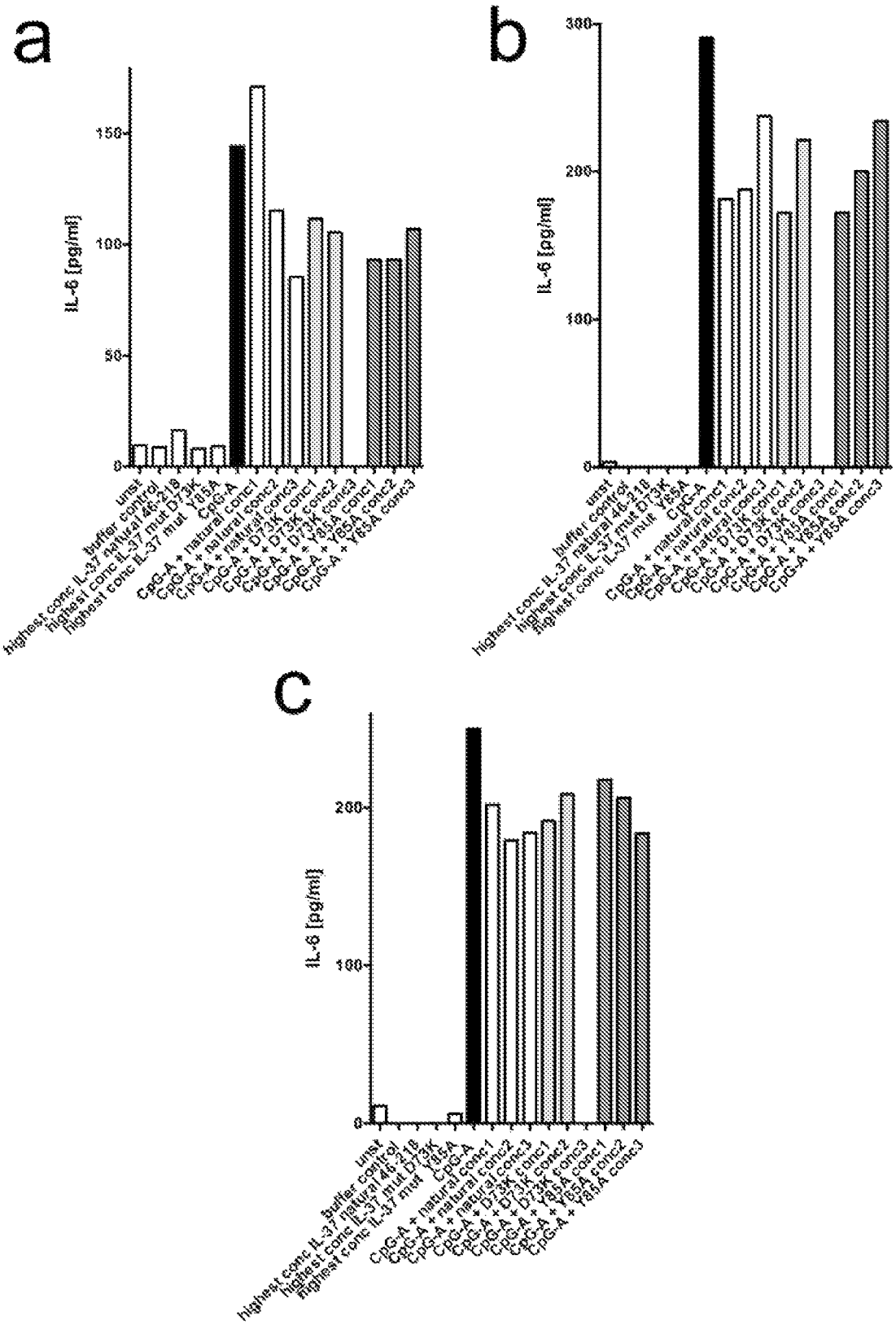
Figure 11:
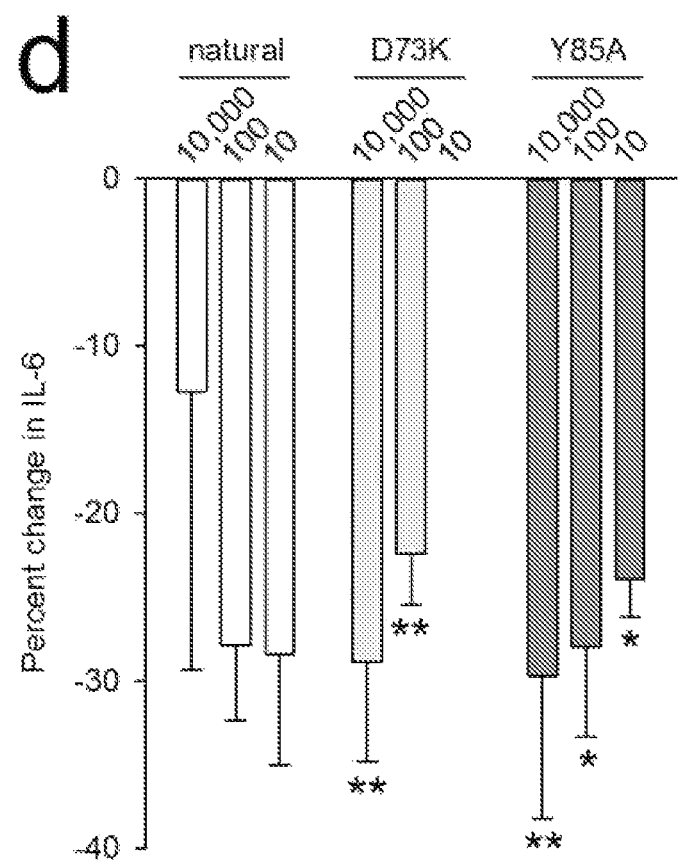

FIG. 11: Freshly isolated PBMC were stimulated as indicated. CpG-A was used at 3 μM and added 30 min after the recIL-37b variants. Black, CpG-A alone; white, CpG-A+ natural recIL-37; light grey, CpG-A+D73K; dark grey, CpG-A+Y85A (all variants 46-218). Supernatants were collected 20 h after the addition of CpG-A and IL-6 (a-c) was measured by ELISA. (a-c) Concentration (conc) 1, 10 ng/ml; conc 2, 100 pg/ml; conc 3, 10 pg/ml. Graphs show absolute cytokine concentrations±SEM in the supernatants of the cultures of individual donors FC (a), JM (b), and LM (c). Data for CpG-A+D73K conc 3 not available. (d) Percent change in IL-6 was calculated from the raw data shown in panels a-c and is depicted±SEM. Concentrations of recIL-37 are indicated in pg/ml. *, $P<0.05$; **, $P<0.01$ for CpG-A alone vs CpG-A+ recIL-37.

Figure 12:
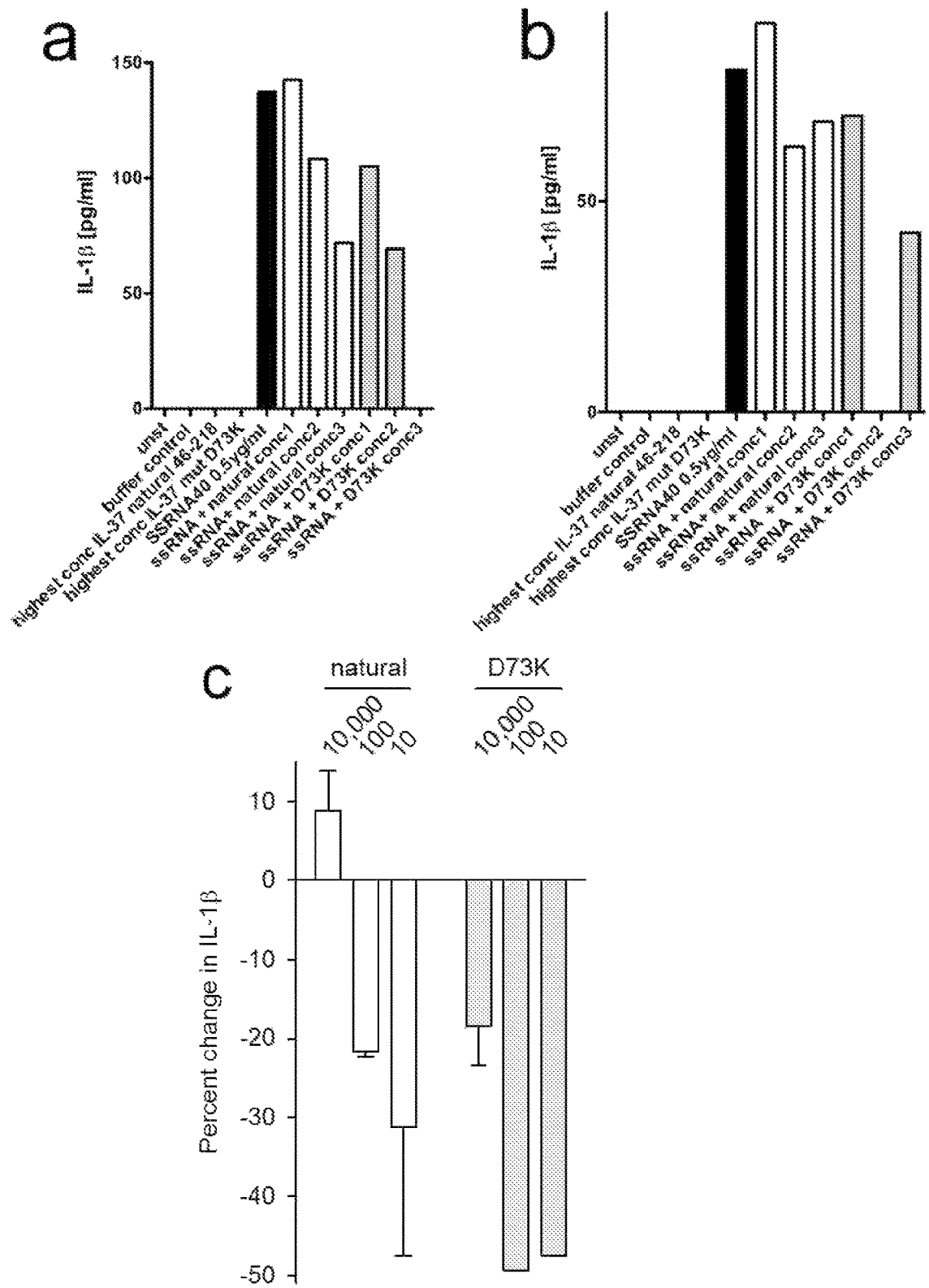

FIG. 12: Freshly isolated PBMC were stimulated as indicated. ssRNA40 was used at 0.5 pg/ml and added 30 min after the recIL-37 variants. Black, ssRNA40 alone; white, ssRNA40+ natural recIL-37; light grey, ssRNA40+D73K; dark grey, ssRNA40+Y85A (all variants 46-218). Supernatants were collected 20 h after the addition of ssRNA40 and IL-1β was measured by ELISA. (a, b) Concentration (conc) 1, 10 ng/ml; conc 2, 100 pg/ml; conc 3, 10 pg/ml. Graphs show absolute cytokine concentrations±SEM in the supernatants of the cultures of individual donors JF (a) and MS (b). Data for ssRNA40+D73K conc 3 (JF) and 2 (MS) are not available. (c) Percent change in IL-1β was calculated from the raw data shown in panels a and b and is

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

The work of the inventors leading to the invention includes the 2.3 Å resolution crystal structure of IL-37 revealing a characteristic IL-1 cytokine p-trefoil fold composed of 12 β-strands and three a-helices. Unexpectedly, IL-37 forms a head-to-head homodimeric arrangement that is unique within the IL-1 superfamily. IL-37 is dimeric in solution, and structure-guided point mutations within the dimer interface convert IL-37 into a monomer. Monomeric IL-37 is significantly more effective at suppressing pro-inflammatory cytokine release in a range of cell types, including human blood cells. Together, these data indicate IL-37 homodimerization constitutes a novel self-regulatory mechanism that tightly control its anti-inflammatory signalling. Significantly, monomeric IL-37 represents a molecule of potential therapeutic benefit in the treatment a range of inflammatory diseases.

The polypeptides of the invention exhibit significantly increased anti-inflammatory activity. An advantage of the polypeptides of the invention is that the efficacy loss that is observed with wildtype (i.e. natural, endogenous) IL-37 at increased concentrations does not occur. In other words, the polypeptides of the invention continue to exhibit anti-inflammatory effects at high concentrations and over, at least, a 4 log concentration range. This is particularly advantageous as the therapeutic window for a polypeptide of the invention is considerably wider compared to wildtype recombinant IL-37.

An IL-37 polypeptide is a molecule that has at least one biochemical or biophysical activity of IL-37, for example, it can bind to, and may be a ligand for interleukin 18 receptor (IL-18R1/IL-1Rrp). It may also bind to interleukin 18 binding protein (IL-18BP), an inhibitory binding protein of interleukin 18 (IL-18), and subsequently form a complex with the IL-18 receptor beta chain, and through which it may inhibit the activity of IL-18. Other biochemical or biophysical activities of IL-37 include binding to IL-1R8 (Sigirr), blocking the production of pro-, but not anti-inflammatory, cytokines triggered by a broad spectrum of inflammatory assaults including TLR ligands, IFNγ, TNF and IL-1β in human or murine immune cells, inhibition of the activation of dendritic cells (reduction of surface expression of CD86 and MHC II), triggering a specific pattern of regulation of intracellular kinases including blockade of the mTOR, MAPK and NF-κB pathways, and induction of anti-inflammatory kinases such as Mer and PTEN (as described in (5)).

IL-37 is also known as interleukin-37 (FIL1 zeta; IL-1 zeta; IL-1F7b (IL-1H4, IL-1H, IL-1RP1); IL-1X protein; IL1F7 (canonical product IL-1F7b); interleukin 1 family member 7; interleukin 1, zeta; interleukin-1 homolog 4; interleukin-1 superfamily z; interleukin-1-related protein and interleukin-23). Human IL-37 has 5 isoforms, a, b, c, d and e, all of which are included when referring to IL-37 herein unless expressly stated otherwise. Any isoforms or orthologs of human IL-37 polypeptides which contain at least one residue equivalent to a dimer interface residue in Table 1 are also contemplated within the present invention. For example, the present invention includes polypeptides with identity to any of human IL-37 isoforms a, b, c, d or e.

A dimerization interface that enables dimerization of IL-37 monomers refers to the interface between two IL-37 molecules which is involved in the binding of one molecule to the other. Typically the interface is not solvent accessible when the two molecules are interacting. The interface includes residues that make critical interactions and/or contribute to the buried surface area of the interface. The interface may be the same or different in terms of surface area size or residue composition on each molecule in the interaction. The interface includes any one or more of the residues listed in Table 1 below that make critical interactions and/or contribute to the buried surface area of the interface. The β3-β4 loop (residues 83-91) is a critical region of secondary structure that controls dimerization. Other regions also contribute to the interface. Y85 packs onto a hydrophobic surface formed by Val71, Val80 and Ile78. The burying of Y85 into this surface region would appear critical to dimer formation as mutation of the sidechain to alanine ablates the dimer.

TABLE 1

Residues that contribute to the IL-37 dimer interface are listed. Any one or more of these are residues that could be genetically/chemically modified to interfere with IL-37 dimerization. Data derived from PDBePISA (EMBL).

| IL37 chain: residue | Interaction type | Buried surface area Å$^2$ |
|---|---|---|
| A: Val 71 | | 19.40 |
| A: Leu 72 | | 26.67 |
| A: Asp 73 | Hydrogen-bond | 48.69 |
| A: Ser 74 | | 5.24 |
| A: Ile 78 | | 7.20 |
| A: Val 80 | | 9.87 |
| A: Lys 83 | Hydrogen-bond, salt-bridge | 38.18 |
| A: Asn 84 | | 31.96 |
| A: Tyr 85 | Hydrogen-bond | 150.42 |
| A: Ile 86 | Hydrogen-bond | 34.53 |
| A: Arg 87 | Hydrogen-bond | 109.21 |
| A: Pro 88 | | 2.35 |
| A: Asn 184 | | 3.26 |
| B: Val 71 | | 21.09 |
| B: Leu 72 | | 19.75 |

TABLE 1-continued

Residues that contribute to the IL-37 dimer interface are listed. Any one or more of these are residues that could be genetically/chemically modified to interfere with IL-37 dimerization. Data derived from PDBePISA (EMBL).

| IL37 chain: residue | Interaction type | Buried surface area Å$^2$ |
|---|---|---|
| B: Asp 73 | Salt-bridge | 42.84 |
| B: Ser 74 | Hydrogen-bond | 10.20 |
| B: Ile 78 | | 6.02 |
| B: Val 80 | | 7.70 |
| B: Lys 83 | | 18.06 |
| B: Asn 84 | Hydrogen-bond | 49.36 |
| B: Tyr 85 | Hydrogen-bond | 143.82 |
| B: Ile 86 | Hydrogen-bond | 35.73 |
| B: Arg 87 | Hydrogen-bond | 106.58 |
| B: Pro 88 | | 10.71 |
| B: Asn 184 | | 6.06 |

A mutation or modification of any one or more of the residues in Table 1 that reduces or inhibits its capacity to be involved in the specific interaction type is also contemplated. For example, any mutation at, or a position equivalent to, Asp73 that reduces or inhibits the capacity to form a salt-bridge is included in the present invention. The same applies to the hydrogen-bonds formed by Ser74, Asn84, Tyr85, Ile86 and Arg87.

Any modification of β3-β4 loop (residues 83-91) region could shift the equilibrium from dimer to monomer. That includes, but would not be limited to, deleting the loop, shortening the loop, lengthening the loop, mutating residues of the loop and/or chemically modifying loop residues. Within the loop region Lys83, Asn84, Tyr85, Ile86, Arg87 and Pro88 appear the most critical residues and are therefore considered for mutation or modification.

The present invention also provides a compound that inhibits dimerization of an IL-37 polypeptide. Preferably, the compound binds to and/or disrupts the dimerization interface. The compound may be a peptide, peptidomimetic, antibody or small molecule that interacts with a least one amino acid residue in the dimerization interface.

Further, the present invention also provides use of a compound that inhibits dimerization of an IL-37 polypeptide in the manufacture of a medicament for inhibiting inflammation. Also, the present invention provides a method of inhibiting inflammation in a subject in need thereof, comprising administering a compound that inhibits dimerization of an IL-37 polypeptide. Preferably, the compound binds to and disrupts the dimerization interface. The compound may be a peptide, peptidomimetic, antibody or small molecule that interacts with a least one amino acid residue in the dimerization interface.

The present invention also provides a peptide comprising, consisting essentially of or consisting of at least 5, 6, 7, 8, 9, 10, 11, 12, 13, 14, 15, 16, 17 or 18 contiguous amino acids of the amino acid sequence of the dimerization interface of SEQ ID NO: 1. Preferably, the contiguous amino acids are from V71 to P88 of SEQ ID NO: 1. The peptide may be used to generate antibodies that can inhibit dimerization of an IL-37 polypeptide.

As used herein an amino acid residue at the position equivalent to position in SEQ ID NO: 1 can be determined by any means known to a person skilled in the art. For example, an alignment of one or more sequences with an amino acid sequence of SEQ ID NO: 1 would allow a person skilled in the art to determine the amino acid at the position equivalent to position in SEQ ID NO: 1. A person skilled in the art can compare the three dimensional structure of a polypeptide with the three dimensional structure of a polypeptide having the amino acid sequence of SEQ ID NO: 1 and determine the amino acid residue that is at an equivalent position to that in SEQ ID NO: 1.

As used herein "reduced capacity to form a dimer" refers to a lesser propensity for a polypeptide to form a homodimer and/or heterodimer compared to a reference polypeptide. The capacity for a polypeptide to form a dimer may be measured via various means including those methods described herein, such as size exclusion chromatography and multi-angle light scattering. Preferably, a polypeptide that has a reduced capacity to form a dimer has at least about a 10%, 20%, 30%, 40%, 50%, 60%, 70%, 80%, 90% or 100% reduction in dimer formation compared to a reference polypeptide. The reference polypeptide will typically be a native, wildtype, unmodified or unmutated polypeptide. For the assessment of the proportion of a polypeptide present in a given form, i.e. a monomer or dimer, a suitable method is, for example, analytical gel electrophoresis under non-denaturing conditions. In such a method, a solution of the polypeptide is run in a polyacrylamide gel, alongside a set of standard molecular weight markers. If the polypeptide forms dimers, a protein band will be observed in the gel corresponding to a species with a molecular weight approximately twice that calculated for the sum of the amino acids of the polypeptide. A second band may also be observed corresponding to a species with approximately the molecular weight calculated for the sum of the amino acids of the polypeptide—this represents the sequence in monomeric form. The relative intensities of the bands may be used to quantify the proportion of the polypeptide which is present in each form. Similar methods may assess molecular weight by alternative means, for example, analytical centrifugation, mass spectrometry or size exclusion chromatography. Alternatively, monomers or dimers may be quantified using reverse phase high performance liquid chromatography (RP-HPLC) where the dimers and higher oligomeric species are separated from the monomers based on differences in their hydrophobicities. Identification of the species may be achieved using mass spectrometric detection. The same methods may be adapted to assess whether a given polypeptide shows a tendency to heterodimerise or homodimerise.

The anti-inflammatory properties of a polypeptide of the invention can be determined by any method described herein, particular in the Examples.

"Isolated," when used to describe the various polypeptides disclosed herein, means the polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes polypeptide in situ within recombinant cells, since at least one component of the polypeptide natural environment will not be present. Ordinarily, however, isolated polypeptide will be prepared by at least one purification step.

A "fragment" is a portion of a polypeptide of the present invention that retains substantially similar functional activity or substantially the same biological function or activity as the polypeptide, which can be determined using assays described herein.

"Percent (%) amino acid sequence identity" or "percent (%) identical" with respect to a polypeptide sequence, i.e. a polypeptide of the invention defined herein, is defined as the percentage of amino acid residues in a candidate sequence that are identical with the amino acid residues in the specific polypeptide of the invention, after aligning the sequences and introducing gaps, if necessary, to achieve the maximum percent sequence identity, and not considering any conservative substitutions as part of the sequence identity.

Those skilled in the art can determine appropriate parameters for measuring alignment, including any algorithms (non-limiting examples described below) needed to achieve maximal alignment over the full-length of the sequences being compared. When amino acid sequences are aligned, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) can be calculated as: percent amino acid sequence identity=X/Y100, where X is the number of amino acid residues scored as identical matches by the sequence alignment program's or algorithm's alignment of A and B and Y is the total number of amino acid residues in B. If the length of amino acid sequence A is not equal to the length of amino acid sequence B, the percent amino acid sequence identity of A to B will not equal the percent amino acid sequence identity of B to A.

In calculating percent identity, typically exact matches are counted. The determination of percent identity between two sequences can be accomplished using a mathematical algorithm. A nonlimiting example of a mathematical algorithm utilized for the comparison of two sequences is the algorithm of Karlin and Altschul (1990) Proc. Natl. Acad. Sci. USA 87:2264, modified as in Karlin and Altschul (1993) Proc. Natl. Acad. Sci. USA 90:5873-5877. Such an algorithm is incorporated into the BLASTN and BLASTX programs of Altschul et al. (1.990) Mol. Biol. 215:403. To obtain gapped alignments for comparison purposes, Gapped BLAST (in BLAST 2.0) can be utilized as described in Altschul et al. (1997) Nucleic Acids Res. 25:3389. Alternatively, PSI-Blast can be used to perform an iterated search that detects distant relationships between molecules. See Altschul et al. (1997) supra. When utilizing BLAST, Gapped. BLAST, and PSI-Blast programs, the default parameters of the respective programs (e.g., BLASTX and BLASTN) can be used. Alignment may also be performed manually by inspection. Another non- limiting example of a mathematical algorithm utilized for the comparison of sequences is the ClustalW algorithm (Higgins et al. (1994) Nucleic Acids Res. 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting examples of a software program useful for analysis of ClustalW alignments is GENEDOC™ or JalView. GENEDOC™ allows assessment of amino acid (or DNA) similarity and identity between multiple proteins. Another non- limiting example of a mathematical algorithm utilized for the comparison of sequences is the algorithm of Myers and Miller (1988) CABIOS 4: 1 1-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM 120 weight residue table, a gap length penalty of 12, and a gap penalty of 4 can be used.

The polypeptide desirably comprises an amino end and a carboxyl end. The polypeptide can comprise D-amino acids, L-amino acids or a mixture of D- and L-amino acids. The D-form of the amino acids, however, is particularly preferred since a polypeptide comprised of D-amino acids is expected to have a greater retention of its biological activity in vivo.

The polypeptide can be prepared by any of a number of conventional techniques. The polypeptide can be isolated or purified from a naturally occurring source or from a recombinant source. Recombinant production is preferred. For instance, in the case of recombinant polypeptides, a DNA fragment encoding a desired peptide can be subcloned into an appropriate vector using well-known molecular genetic techniques (see, e.g., Maniatis et al., Molecular Cloning: A Laboratory Manual, 2nd ed. (Cold Spring Harbor Laboratory, 1982); Sambrook et al., Molecular Cloning A Laboratory Manual, 2nd ed. (Cold Spring Harbor Laboratory, 1989). The fragment can be transcribed and the polypeptide subsequently translated in vitro. Commercially available kits also can be employed (e.g., such as manufactured by Clontech, Palo Alto, Calif.; Amersham Pharmacia Biotech Inc., Piscataway, N.J.; InVitrogen, Carlsbad, Calif., and the like). The polymerase chain reaction optionally can be employed in the manipulation of nucleic acids.

The term "conservative substitution" as used herein, refers to the replacement of an amino acid present in the native sequence in the peptide with a naturally or non-naturally occurring amino acid or a peptidomimetic having similar steric properties. Where the side-chain of the native amino acid to be replaced is either polar or hydrophobic, the conservative substitution should be with a naturally occurring amino acid, a non- naturally occurring amino acid or with a peptidomimetic moiety which is also polar or hydrophobic (in addition to having the same steric properties as the side-chain of the replaced amino acid).

Conservative amino acid substitution tables providing functionally similar amino acids are well known to one of ordinary skill in the art. The following six groups are examples of amino acids that may be considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

As naturally occurring amino acids are typically grouped according to their properties, conservative substitutions by naturally occurring amino acids can be determined bearing in mind the fact that replacement of charged amino acids by sterically similar non-charged amino acids are considered as conservative substitutions. For producing conservative substitutions by non-naturally occurring amino acids it is also possible to use amino acid analogs (synthetic amino acids) well known in the art. A peptidomimetic of the naturally occurring amino acid is well documented in the literature known to the skilled person and non-natural or unnatural amino acids are described further below. When affecting conservative substitutions the substituting amino acid should have the same or a similar functional group in the side chain as the original amino acid.

The phrase "non-conservative substitution" or a "non-conservative residue" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH2)5-COOH]—CO— for aspartic acid. Non-conservative substitution includes any mutation that is not considered conservative.

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl.

Alterations of the native amino acid sequence to produce mutant polypeptides, such as by insertion, deletion and/or substitution, can be done by a variety of means known to those skilled in the art. For instance, site-specific mutations can be introduced by ligating into an expression vector a synthesized oligonucleotide comprising the modified site. Alternately, oligonucleotide-directed site-specific mutagenesis procedures can be used, such as disclosed in Walder et al., Gene 42: 133 (1986); Bauer et al., Gene 37: 73 (1985); Craik, Biotechniques, 12-19 (January 1995); and U.S. Pat. Nos. 4,518,584 and 4,737,462. A preferred means for introducing mutations is the QuikChange Site-Directed Mutagenesis Kit (Stratagene, LaJolla, Calif.).

Any appropriate expression vector (e.g., as described in Pouwels et al., Cloning Vectors: A Laboratory Manual (Elsevier, N.Y.: 1985)) and corresponding suitable host can be employed for production of recombinant polypeptides. Expression hosts include, but are not limited to, bacterial species within the genera *Escherichia, Bacillus, Pseudomonas, Salmonella*, mammalian or insect host cell systems including baculovirus systems (e.g., as described by Luckow et al., Bio/Technology 6: 47 (1988)), and established cell lines such as the COS-7, C127, 3T3, CHO, HeLa, and BHK cell lines, and the like. The skilled person is aware that the choice of expression host has ramifications for the type of polypeptide produced. For instance, the glycosylation of polypeptides produced in yeast or mammalian cells (e.g., COS-7 cells) will differ from that of polypeptides produced in bacterial cells, such as *Escherichia coli*.

Alternately, a polypeptide of the invention can be synthesized using standard peptide synthesizing techniques well-known to those of ordinary skill in the art (e.g., as summarized in Bodanszky, Principles of Peptide Synthesis (Springer-Verlag, Heidelberg: 1984)). In particular, the polypeptide can be synthesized using the procedure of solid-phase synthesis (see, e.g., Merrifield, J. Am. Chem. Soc. 85: 2149-54 (1963); Barany et al., Int. J. Peptide Protein Res. 30: 705-739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The polypeptide-containing mixture can then be extracted, for instance, with dimethyl ether, to remove non-peptidic organic compounds, and the synthesized polypeptide can be extracted from the resin powder (e.g., with about 25% w/v acetic acid). Following the synthesis of the polypeptide, further purification (e.g., using high performance liquid chromatography (HPLC)) optionally can be done in order to eliminate any incomplete polypeptides or free amino acids. Amino acid and/or HPLC analysis can be performed on the synthesized polypeptide to validate its identity. For other applications according to the invention, it may be preferable to produce the polypeptide as part of a larger fusion protein, such as by the methods described herein or other genetic means, or as part of a larger conjugate, such as through physical or chemical conjugation, as known to those of ordinary skill in the art and described herein.

A polypeptide of the invention may also be modified by, conjugated or fused to another moiety to facilitate purification, or increasing the in vivo half-life of the polypeptides, or for use in immunoassays using methods known in the art. For example, a polypeptide of the invention may be modified by glycosylation, acetylation, pegylation, phosphorylation, amidation, derivatization by known protecting/blocking groups, proteolytic cleavage, linkage to a cellular ligand or other protein, etc.

A "peptidomimetic" is a synthetic chemical compound that has substantially the same structure and/or functional characteristics of a polypeptide of the invention, the latter being described further herein. Typically, a peptidomimetic has the same or similar structure as a polypeptide of the invention, for example the same or similar sequence of SEQ ID NO: 1 or fragment thereof that has a reduced capacity to form a dimer. A peptidomimetic generally contains at least one residue that is not naturally synthesised. Non-natural components of peptidomimetic compounds may be according to one or more of: a) residue linkage groups other than the natural amide bond ('peptide bond') linkages; b) non-natural residues in place of naturally occurring amino acid residues; or c) residues which induce secondary structural mimicry, i.e, to induce or stabilize a secondary structure, e.g., a beta turn, gamma turn, beta sheet, alpha helix conformation, and the like.

Peptidomimetics can be synthesized using a variety of procedures and methodologies described in the scientific and patent literatures, e.g., Organic Syntheses Collective Volumes, Gilman et al. (Eds) John Wiley & Sons, Inc., NY, al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymot. 267: 220-234

Modifications contemplated herein include, but are not limited to, modification to side chains, incorporating of unnatural amino acids and/or their derivatives during polypeptide synthesis and the use of crosslinkers and other methods which impose conformational constraints on the polypeptides of the invention. Any modification, including post-translational modification, that reduces the capacity of the molecule to form a dimer is contemplated herein. An example includes modification incorporated by click chemistry as known in the art. Exemplary modifications include PEGylation and glycosylation.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids contemplated herein is shown in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |

TABLE 2-continued

| Non-conventional amino acid | Code | Non-conventional amino acid | Code |
|---|---|---|---|
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenyl-ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

Nucleic acid molecules that encode any of the polypeptides of the invention are also within the scope of the invention. The nucleic acids are useful, for example, in making the polypeptides of the present invention and as therapeutic agents. They may be administered to cells in culture or in vivo and may include a secretory signal that directs or facilitates secretion of the polypeptide of the invention from the cell. Also within the scope of the invention are expression vectors and host cells that contain or include nucleic acids of the invention (described further below). While the nucleic acids of the invention may be referred to as "isolated," by definition, the polypeptides of the invention are not wild-type polypeptides and, as such, would not be encoded by naturally occurring nucleic acids. Thus, while the polypeptides and nucleic acids of the present invention may be "purified," "substantially purified," "isolated," "recombinant" or "synthetic" they need not be so in order to be distinguished from naturally occurring materials.

An "isolated" nucleic acid molecule is a nucleic acid molecule that is identified and separated from at least one contaminant nucleic acid molecule with which it is ordinarily associated in the natural source of the polypeptide encoding, typically IL-37, nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes nucleic acid molecules contained in cells that ordinarily express IL-37 where, for example, the nucleic acid molecule is in a chromosomal location different from that of natural cells.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides of the invention can be synthesised according to methods well known in the art, as described by way of example in Sambrook et al (1989, Molecular Cloning—a laboratory manual; Cold Spring Harbor Press).

The polynucleotide molecules of the present invention may be provided in the form of an expression cassette which includes control sequences operably linked to the inserted sequence, thus allowing for expression of the polypeptide of the invention in vivo in a targeted subject. These expression cassettes, in turn, are typically provided within vectors (e.g., plasmids or recombinant viral vectors) which are suitable for use as reagents for nucleic acid immunization. Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Thus, the present invention provides a vector for use in preventing or treating an inflammatory disease or condition comprising a polynucleotide sequence which encodes a polypeptide of the invention and optionally one or more further polynucleotide sequences which encode different polypeptides as defined herein.

Furthermore, it will be appreciated that the compositions and products of the invention may comprise a mixture of polypeptides and polynucleotides. Accordingly, the invention provides a composition or product as defined herein, wherein in place of any one of the polypeptide is a polynucleotide capable of expressing said polypeptide.

Expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

Thus, a polypeptide of the invention may be provided by delivering such a vector to a cell and allowing transcription from the vector to occur. Preferably, a polynucleotide of the invention or for use in the invention in a vector is operably linked to a control sequence which is capable of providing for the expression of the coding sequence by the host cell, i.e. the vector is an expression vector.

"Operably linked" refers to an arrangement of elements wherein the components so described are configured so as to perform their usual function. Thus, a given regulatory sequence, such as a promoter, operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

A number of expression systems have been described in the art, each of which typically consists of a vector containing a gene or nucleotide sequence of interest operably linked to expression control sequences. These control sequences include transcriptional promoter sequences and transcriptional start and termination sequences. The vectors of the invention may be for example, plasmid, virus or phage vectors provided with an origin of replication, optionally a promoter for the expression of the said polynucleotide and optionally a regulator of the promoter. A "plasmid" is a vector in the form of an extra-chromosomal genetic element. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

A polynucleotide, expression cassette or vector according to the present invention may additionally comprise a signal peptide sequence. The signal peptide sequence is generally inserted in operable linkage with the promoter such that the signal peptide is expressed and facilitates secretion of a polypeptide encoded by coding sequence also in operable linkage with the promoter.

Typically a signal peptide sequence encodes a peptide of 10 to 30 amino acids for example 15 to 20 amino acids. Often the amino acids are predominantly hydrophobic. In a typical situation, a signal peptide targets a growing polypeptide chain bearing the signal peptide to the endoplasmic reticulum of the expressing cell. The signal peptide is cleaved off in the endoplasmic reticulum, allowing for secretion of the polypeptide via the Golgi apparatus. Thus, a peptide of the invention may be provided to an individual by expression from cells within the individual, and secretion from those cells.

The phrase "therapeutically effective amount" generally refers to an amount of one or more polypeptides or polynucleotides of the invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein.

The invention finds application in the treatment of various inflammatory diseases or conditions. As used herein, 'inflammatory disease or condition' includes acute or chronic inflammation and inflammatory disorders such as inflammation associated with autoimmune diseases, cardiovascular inflammation (e.g., atherosclerosis, stroke), gastrointestinal inflammation, hepatic inflammatory disorders, pulmonary inflammation (e.g. asthma, ventilator induced lung injury), kidney inflammation, ocular inflammation (e.g., uveitis), pancreatic inflammation, genitourinary inflammation, neuroinflammatory disorders (e.g., multiple sclerosis, Alzheimer's disease), allergy (e.g., allergic rhinitis/sinusitis, skin allergies and disorders (e.g., urticaria/hives, angioedema, atopic dermatitis, contact dermatitis, psoriasis), food allergies, drug allergies, insect allergies, mastocytosis), skeletal inflammation (e.g., arthritis, osteoarthritis, rheumatoid arthritis, spondyloarthropathies), infection (e.g., bacterial or viral infections; oral inflammatory disorders (i.e., perodontis, gingivitis or somatitis); and transplantation (e.g., allograft or xenograft rejection, maternal-fetal tolerance, graft-versus-host disease).

The invention finds application in the treatment of various inflammatory diseases or conditions for which treatment with recombinant wildtype IL-37 has been suggest, for example the diseases or conditions referred to in Dinarello et al. Eur. J. Immunol. (2016) 46: 1067-1081, particularly, Table 3.

The inflammatory disease or condition contemplated for treatment in a method or use of the invention, or by a polypeptide or pharmaceutical composition of the invention, include those predominantly mediated by activation of Toll-like receptor (TLR) 2, 4, 7, 8 and/or 9. A summary of those diseases and conditions associated with TLR activation can be found in FIG. 1 and Table 1 in Connolly et al Current Opinion in Pharmacology 2012, 12:510-518. Exemplary indications contemplated for treatment by a method or use of the invention, or by a polypeptide or pharmaceutical composition of the invention, and the TLR that predominantly mediates the inflammation of that indication are:

Ischemia/reperfusion injury, cardiac ischemia, delayed graft function (TLR 2);
Rheumatoid arthritis (TLR 2);
Systemic Lupus erythematosus (TLR7, 8 and/or 9);
Sepsis (TLR 4 among other TLRs); and
Acute and chronic inflammation (TLR 4).

A method or use of the invention, or by a polypeptide or pharmaceutical composition of the invention, find application to reduce, inhibit or prevent inflammation induced by other mediators such as other cytokines (IL-1, IFNγ etc), other mediators (e.g. complement, leukotrienes etc) and chemical and physical insults.

Autoimmune diseases include, for example, Acquired Immunodeficiency Syndrome (AIDS, which is a viral disease with an autoimmune component), alopecia areata, ankylosing, spondylitis, antiphospholipid syndrome, autoimmune Addison's disease, autoimmune haemolytic, anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune, dysfunction syndrome (CFIDS), chronic inflammatory demyelinating polyneuropathy (CIPD), cicatricial pemphigoid, cold agglutinin disease, crest syndrome, Crohn's disease, Degos' disease, dermatomyositis-juvenile, discoid lupus, essential mixed cryoglobulinemia, fibromyalgiafibromyositis, Graves' disease, Guillain-Barre syndrome, Hashimoto's thyroiditis, idiopathic pulmonary fibrosis, idiopathic thrombocytopenia purpura (ITP), IgA nephropathy, insulin dependent diabetes mellitus, juvenile chronic arthritis (Still's disease), juvenile rheumatoid arthritis, Meniere's disease, mixed connective tissue disease, multiple sclerosis, myasthenia gravis, pemacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Preferably, the inflammatory disease or condition is multiple sclerosis, rheumatoid arthritis, skin hypersensitivity such as atopic dermatitis, contact dermatitis, psoriasis, inflammatory bowel disease, uveitis, dry eye disease, Systemic Sclerosis (scleroderma), periodontal disease, vitiligo, SLE/Discoid Lupus/Grave disease, atherosclerosis, asthma, or delayed-type hypersensitivity.

Multiple sclerosis (MS) is an inflammatory disease involving demyelination of myelin sheaths surrounding brain and spinal cord axons. MS symptoms include, but are not limited to scarring of white matter in the brain and/or spinal cord and a wide variety of neurological symptoms, including but not limited to changes in sensation such as loss of sensitivity or tingling, pricking or numbness (hypoesthesia and parasthesia), muscle weakness, clonus, muscle spasms or difficulty in moving; difficulties with coordination and balance (ataxia); problems in speech (dysarthria) or swallowing (dysphagia), visual problems (nystagmus, optic neuritis, etc.), fatigue, acute/chronic pain, and bladder and bowel difficulties. Cognitive impairment of varying degrees and depression are also common. Symptoms of MS usually appear in episodic acute periods of worsening in a gradually progressive deterioration of neurologic function, or in a combination of both.

Rheumatoid arthritis is a chronic systemic inflammatory disorder that may affect many tissues and organs, but principally attacks synovial joints. The process involves an inflammatory response of the synovial capsule around the joints secondary to hyperplasia of synovial cells, excess synovial fluid, and the development of fibrous tissue in the synovia. The pathology of the disease process often leads to the destruction of articular cartilage and ankylosis of the joints. Rheumatoid arthritis can also produce diffuse inflammation in the lungs, pericardium, lung pleura, sclera, and nodular lesions, most common in subcutaneous tissue.

Other inflammatory diseases or conditions include acute inflammation associated with stroke, myocardial infarction, ischemia-reperfusion injury and transplantation. Further, chronic inflammation associated with autoinflammatory diseases or autoimmune diseases, such as multiple sclerosis described above and diabetes (type 1 or type 2 diabetes).

A further inflammatory disease or condition is sepsis, septic shock or endotoxic shock. The sepsis or endotoxic shock may be caused by bacteria, fungi, viruses, or parasites. The causative agent from bacteria may be lipopolysaccharides (LPS), also known as lipoglycans and endotoxins, which are large molecules consisting of a lipid and a polysaccharide composed of O-antigen, outer core and inner core joined by a covalent bond; they are found in the outer membrane of Gram-negative bacteria, and elicit strong immune responses in animals.

For any of the inflammatory diseases or conditions described herein, when the polypeptide of the present invention is topically administered to a human, the therapeutically effective amount of a compound corresponds to preferably between about 0.01 to about 10% (w/w), or between about 0.1 to 10% (w/w), or between about 1.0 to about 10% (w/w), between about 0.1 to about 5% (w/w), or between about 1.0 to about 5% (w/w). In any of the inflammatory diseases or conditions diseases described herein, when the polypeptide of the present invention is orally administered to a subject, the therapeutically effective amount of a compound corresponds preferably between about 1 to about 50 mg/kg, or between about 1 to 25 mg/kg, or between about 1 to about 10 mg/kg, between about 5 to about 25 mg/kg, or between about 10 to about 20 mg/kg.

In a composition of the invention, the proportion of polypeptide of the invention present as a monomer may be at least about 0.5%, 1%, 2%, 3%, 4%, 5%, 6%, 7%, 8%, 9%, 10%, 20%, 30%, 40%, 50%, 60%, 70%, 80% or 90% of the total polypeptide present in the composition, typically stored in solution for a suitable period of time under suitable conditions. Suitable periods of time and conditions include ranges of time and conditions under which a skilled practitioner might reasonably expect to keep a polypeptide in solution prior to use. For example, periods of time of about 24 hours, about 48 hours, or about 72 hours are typical, although some solutions may be kept for longer periods for example, at least a week, a month, 6 months, 1 year, 2 years, 3 years or more. Storage conditions may typically be room temperature and relative humidity, or typically 25° C. and 60% relative humidity, but could include any standard storage conditions encountered by the skilled person, for example approximately 4° C., −20° C., or −80° C.

The frequency of administration may be once daily, or 2 or 3 time daily. The treatment period may be for the duration of the detectable disease.

Typically, a therapeutically effective dosage is formulated to contain a concentration (by weight) of at least about 0.1% up to about 50% or more, and all combinations and subcombinations of ranges therein. The compositions can be formulated to contain one or more polypeptides of the invention in a concentration of from about 0.1 to less than about 50%, for example, about 49, 48, 47, 46, 45, 44, 43, 42, 41 or 40%, with concentrations of from greater than about 0.1%, for example, about 0.2, 0.3, 0.4 or 0.5%, to less than about 40%, for example, about 39, 38, 37, 36, 35, 34, 33, 32, 31 or 30%. Exemplary compositions may contain from about 0.5% to less than about 30%, for example, about 29, 28, 27, 26, 25, 25, 24, 23, 22, 21 or 20%, with concentrations of from greater than about 0.5%, for example, about 0.6, 0.7, 0.8, 0.9 or 1%, to less than about 20%, for example, about 19, 18, 17, 16, 15, 14, 13, 12, 11 or 10%. The compositions can contain from greater than about 1% for example, about 2%, to less than about 10%, for example about 9 or 8%, including concentrations of greater than about 2%, for example, about 3 or 4%, to less than about 8%, for example, about 7 or 6%. The active agent can, for example, be present in a concentration of about 5%. In all cases, amounts may be adjusted to compensate for differences in amounts of active ingredients actually delivered to the treated cells or tissue.

Although the invention finds application in humans, the invention is also useful for therapeutic veterinary purposes. The invention is useful for domestic or farm animals such as cattle, sheep, horses and poultry; for companion animals such as cats and dogs; and for zoo animals.

Pharmaceutical compositions may be formulated for any appropriate route of administration including, for example, topical (for example, transdermal or ocular), oral, buccal, nasal, vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. Within yet other embodiments, compositions provided herein may be formulated as a lyophilizate.

The various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets. The dosage units may further include conventional excipients well-known in pharmaceutical formulation practice, such as binding agents, gellants, fillers, tableting lubricants, disintegrants, surfactants, and colorants; and for suckable or chewable formulations.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Aqueous suspensions contain the active ingredient(s) in admixture with excipients suitable for the manufacture of aqueous suspensions. Such excipients include suspending agents such as sodium carboxymethylcellulose, methylcellulose, hydropropylmethylcellulose, sodium alginate, polyvinylpyrrolidone, gum tragacanth and gum acacia, and dispersing or wetting agents such as naturally-occurring phosphatides (for example, lecithin), condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol mono-oleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil such as arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or *arachis* oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan monoleate, and condensation products of partial esters derived from fatty acids and hexitol with ethylene oxide such as polyoxyethylene sorbitan monoleate. An emulsion may also comprise one or more sweetening and/or flavouring agents.

Syrups and elixirs may be formulated with sweetening agents, such as glycerol, propylene glycol, sorbitol or sucrose. Such formulations may also comprise one or more demulcents, preservatives, flavouring agents and/or colouring agents.

Polypeptides of the invention may be formulated for local or topical administration, such as for topical application to the skin. Formulations for topical administration typically comprise a topical vehicle combined with active agent(s), with or without additional optional components.

Suitable topical vehicles and additional components are well known in the art, and it will be apparent that the choice of a vehicle will depend on the particular physical form and mode of delivery. Topical vehicles include organic solvents such as alcohols (for example, ethanol, iso-propyl alcohol or glycerine), glycols such as butylene, isoprene or propylene glycol, aliphatic alcohols such as lanolin, mixtures of water and organic solvents and mixtures of organic solvents such as alcohol and glycerine, lipid-based materials such as fatty acids, acylglycerols including oils such as mineral oil, and fats of natural or synthetic origin, phosphoglycerides, sphingolipids and waxes, protein-based materials such as collagen and gelatine, silicone-based materials (both nonvolatile and volatile), and hydrocarbon-based materials such as microsponges and polymer matrices.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form. Solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity. Both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels, and often do not contain emulsifiers. Liquid topical products often contain solvents, emulsifiers, moisturizers, emollients, fragrances, dyes/colorants, preservatives and other active ingredients that increase or enhance the efficacy of the final product.

Emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or nonionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylceilulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Typical modes of delivery for topical compositions include application using the fingers, application using a physical applicator such as a cloth, tissue, swab, stick or brush, spraying including mist, aerosol or foam spraying, dropper application, sprinkling, soaking, and rinsing. Controlled release vehicles can also be used, and compositions may be formulated for transdermal administration (for example, as a transdermal patch).

A pharmaceutical composition may be formulated as inhaled formulations, including sprays, mists, or aerosols. This may be particularly preferred for treatment of certain inflammatory diseases or conditions. For inhalation formulations, the composition or combination provided herein may be delivered via any inhalation methods known to a person skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Pharmaceutical compositions may also be prepared in the form of suppositories such as for rectal administration. Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations such as a capsule that creates a slow release of modulator following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of modulator release. The amount of modulator contained within a sustained release formulation depends upon, for example, the site of implantation, the rate and expected duration of release and the nature of the condition to be treated or prevented.

In another embodiment there is provided a kit or article of manufacture including one or more polypeptides or polynucleotides of the invention and/or pharmaceutical composition as described above.

In other embodiments there is provided a kit for use in a therapeutic or prophylactic application mentioned above, the kit including:
 a container holding a polypeptide, polynucleotide or pharmaceutical composition of the invention;
 a label or package insert with instructions for use.

In certain embodiments the kit may contain one or more further active principles or ingredients for treatment of an inflammatory diseases or conditions.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic or prophylactic composition can be used to treat an inflammatory disease or condition described herein.

The kit may comprise (a) a therapeutic or prophylactic composition; and (b) a second container with a second active principle or ingredient contained therein. The kit in this embodiment of the invention may further comprise a package insert indicating the composition and other active principle can be used to treat a disorder or prevent a complication stemming from an inflammatory disease or condition described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the therapeutic, prophylactic or pharmaceutical composition. In one embodiment, the device is a syringe. The device may hold 1-2 mL of the therapeutic composition. The therapeutic or prophylactic composition may be provided in the device in a state that is ready for use or in a state requiring mixing or addition of further components.

A polypeptide or composition of the invention may be used as an anti-inflammatory coating for implantable materials and devices, e.g. stents. The polypeptide or composition of the invention may be coated on to, or integral with, the implantable material or device. The polypeptide or composition of the invention may be part of a polymeric coating.

It will be understood that the invention disclosed and defined in this specification extends to all alternative combinations of two or more of the individual features men-

EXAMPLES

Example 1

Cloning and Protein Purification

Codon optimized IL-37 (46-218) was cloned into a modified tobacco etch virus protease-cleavable version of pGEX-4T-1 (GE Healthcare)(7). Recombinant protein was expressed in BL21-CodonPlus(DE3)-RIL cells (Stratagene) by IPTG induction at 18° C. Cells expressing GST-IL-37 variants were lysed by high-pressure cavitation (10-15 K psi) in 20 mM Tris-HCl (pH 8.0), 500 mM NaCl, 3 mM β-mercaptoethanol, with two complete EDTA-free protease inhibitor tablets (Roche). Cells were clarified by centrifugation, filtered through a 0.45 μm membrane, and bound to glutathione Sepharose 4B resin (GE Healthcare) for 1 h at 4° C. The resin was washed with 500 ml of 20 mM Tris-HCl (pH 8.0), 200 mM NaCl, and 3 mM β-mercaptoethanol. The protein was released from the GST-tag by overnight incubation with His-TEV protease at 4° C. Protein was further purified on a HiLoad Superdex75 16/60 prep-grade column (GE Healthcare) in 20 mM Hepes (pH 7.2), 100 mM NaCl, 2 mM DTT, and 1 mM EDTA.

Crystallization and Structure Determination

IL-37 crystals were grown at 20° C. by hanging drop vapour diffusion in 2.1 M ammonium sulfate and 0.1 M sodium acetate (pH 4.5) at a 1:1 drop ratio. Crystals were flash cooled in liquid nitrogen in mother liquor containing 20% (v/v) glycerol. X-ray data were collected at the MX2 beamline (microfocus) of the Australian Synchrotron at a wavelength of 0.9537 Å with 1° oscillations. Data were processed and scaled using XDS and programs within the CCP4 suite (8). The structure was solved by molecular replacement using murine IL-F5 (PDB code 1MD6 (9)) as the search model in PHENIX using MRage and Phaser (10, 11). The structure was automatically built in PHENIX AutoBuild (11). Iterative cycles of refinement were carried out using Buster (12) with local rebuilding in COOT (13), resulting in a model with an R-factor of 18.22% ($R_{free}$ of 21.74%) and excellent geometry (Table 3). The structure had no Ramachandran outliers with 98.64% of residues in favored regions and a final MolProbity score of 0.95 ($100^{th}$ percentile) (14).

Size exclusion chromatography and multi-angle light scattering (SEC-MALS)

SEC-MALS measurements were carried out on a Superdex75 10/300 column (GE Healthcare) equilibrated in 10 mM HEPES (pH 7.3), 100 mM NaCl, 1 mM EDTA and 2 mM DTT. All experiments were conducted at 25° C. at a flow rate of 0.4 mL/min in the above buffer. A volume of 110 μL of protein at 6 mg/mL was injected for each run. Test injections of 2 mg/ml bovine serum albumin (Thermo Scientific Pierce) were used for calibration purposes. The SEC-MALS system comprised a Shimadzu DGU-20A$_5$ degasser, LC-20AD liquid chromatograph, SIL-20A$_{HT}$ autosampler, CBM-20A communications bus module, SPD-20A UV/VIS detector and CTO-20AC column oven, which was coupled to a DAWN HELEO-II multi-angle light scattering detector fitted with an Optilab T-rEX refractive index detector (Wyatt Technology). Molar masses were calculated by measuring the intensity of scattered light at 18 different scattering angles. Molecular mass calculations were performed using Astra 6.1 software (Wyatt Technology).

Cell Culture and Transfections.

PBMC Experiments were approved by the Monash Health Human Research Ethics Committee B, and were performed with explicit written consent form all volunteers. PBMC were isolated from peripheral venous blood of healthy volunteers by density gradient centrifugation as described (15). PBMCs were plated in RPMI medium containing 1% v/v human serum and 1:500 MycoZap PR, then pre-treated for 30 min with either vehicle or rec IL-37 as indicated, before stimulation with 50 pg/ml LPS, or HKLM, imiquimod, CpG-A or ssRNA40 at concentrations described herein, for 20 h. Supernatants were then subjected to cytokine analysis. THP-1 cells were sourced from the ATCC. They were always cultured in the presence of MycoZap Plus-CL (Lonza), which contains an antibiotic, an antifungal, and an anti-mycoplasmal agent.

THP 1 cells were transfected with constructs encoding the natural IL-37b protein or the monomeric D73K variant as described in (16, 1 and 5). Briefly, each IL 37b variant was inserted into a pIRES vector with a GFP expression sequence and a constitutively active CMV promoter, and the C-terminus of IL 37b was ligated to FLAG. Cells were transfected using the Amaxa Nucleofector Kit V (THP 1) and program V001, followed by an overnight recovery. Twenty hours after transfection, cells were counted and plated. Transfected THP 1 cells were differentiated into macrophages by incubation with 50 ng/ml of PMA for 24 h. Thereafter, the medium was changed to RPMI with penicillin/streptomycin and 1% human serum and the stimuli were added. After the incubation period indicated in the figure legend, supernatants were collected and stored at −80° C. until analysis. Sample collection and analysis were conducted in a blinded manner.

ELISAs and Multiplex ELISAs.

Cytokines were measured by conventional ELISAs (BD, elisakit.com). Both ELISA methods were performed as recommended by the manufacturers.

Statistical Analysis.

Datasets (raw data) were first tested for normality and equal variance (P-value to reject=0.05) using SigmaPlot 12.5 (Systat Software Inc.). Thereafter, the appropriate statistical test was applied, which included unpaired t-tests (two-tailed, $\alpha$=0.05), Mann-Whitney rank sum tests, one way ANOVA, or one way ANOVA on ranks.

Animal Experiments.

All procedures involving mice were approved by the Monash Health Animal Ethics Committee. C57Bl/6 wild-type mice received intraperitoneal injections of 40 μg/kg of the recombinant IL-37 variants or vehicle, followed 60 min later by intraperitoneal injection of LPS (10 mg/kg). Homozygous mice transgenic for IL-37b (1, 5) were also treated with LPS (10 mg/kg) or vehicle for direct comparison. Room temperature and humidity were monitored continuously. Body temperature was measured as described in (1). 24 h after LPS injections, mice were anesthetized and plasma was obtained by orbital bleeding into heparinized tubes.

Reagents

Human IL-1β(beta) ELISA: Cat #, 557953, human IL-6 ELISA, Cat #: 555220, murine IL-1β(beta) ELISA, Cat #: 559603 (BD Biosciences, New Jersey, USA), LPS from *E. Coli* 055:85, #L4005-100 mg (Sigma, St Louis Mo., USA), CpG-A ODN 2216 Innaxon #INAX-200-005 (Adipogen, Switzerland), imiquimod VacciGrade #vac-img, HKLM #Tlrl-hklm, (Invivogen, San Diego, Calif., USA).

Example 2

Precursor and Mature IL-37 Form Homodimers in Solution

Figure 1A:
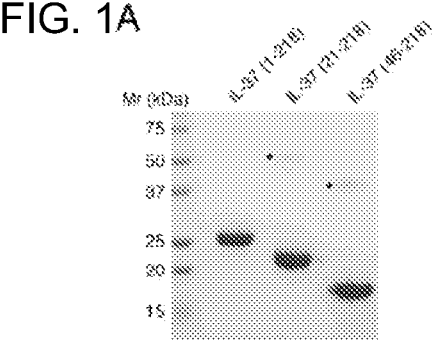
FIGS. 1A-C: IL-37 forms a novel head-to-head symmetrical homodimer.
Figure 1B:
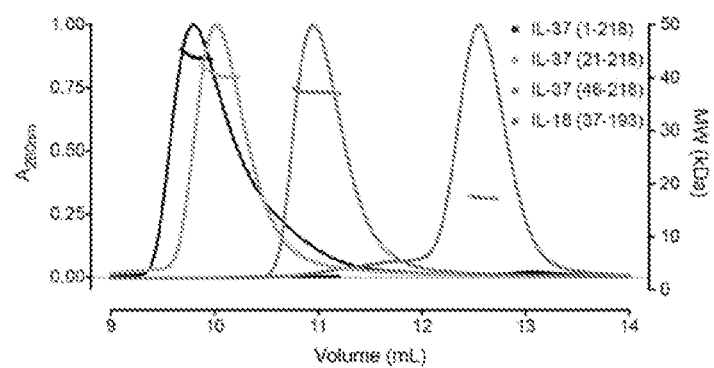

Size exclusion chromatography (SEC) analysis of bacterially purified precursor IL-37 (isoform b, referred to herein as IL-37) indicated that the protein forms a homodimer in solution (FIGS. 1A and 1B, left axis). In order to confirm that the protein was a homodimer, multi-angle light scattering (MALS) coupled to SEC (FIG. 1B, right axis) was carried out. Precursor IL-37 (residues 1-218) had a measured molecular weight of 43.9 kDa consistent with the theoretical molecular weight of 48 kDa for an IL-37 dimer. These data correlate with previous studies that detected dimeric IL-37 (~45 kDa) in human PBMCs and by ultracentrifugation of recombinant IL-37 (1, 2). In FIG. 1B, IL-37 (1-218) elutes at 9.8 ml, IL-37 (21-218) elutes at 10 ml, IL-37 (46-218) elutes at 11 ml and IL-1β (37-193) elutes at 12.6 ml.

To investigate whether N-terminal truncation from the precursor to the mature form prevented dimerization, IL-37 (residues 21-218) and IL-37 (residues 46-218) was purified from bacterial cells and carried out MALS analysis (FIGS. 1A and 1B). Mature IL-37 (21-218) and IL-37 (46-218) each formed dimers in solution with molecular weights of 40.7 kDa and 37.3 kDa, respectively. In comparison to IL-37, mature IL-18 (residues 37-193) had a measured molecular weight of 17.3 kDa consistent with a monomeric structure (FIG. 1B) (3).

Crystal Structure of the IL-37 Homodimer

Figure 1C:
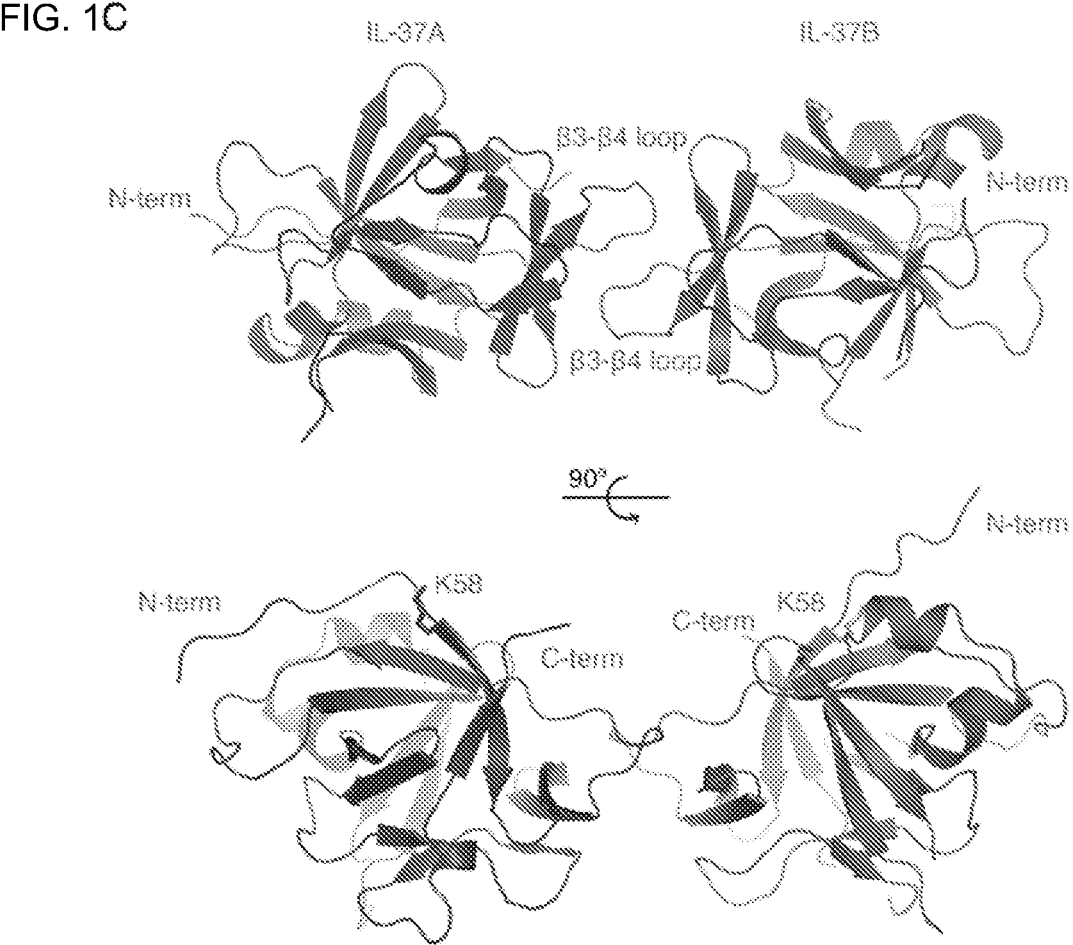

To resolve the molecular basis of IL-37 dimerization mature IL-37 (residues 46-218) was crystallized by hanging drop vapour diffusion. The structure was solved by molecular replacement and refined to 2.3 Å resolution with a $R_{work}/R_{free}$ of 18.22% and 21.74% respectively, and excellent geometry (Table 3). The asymmetric unit contains two copies of IL-37, termed IL-37A and IL-37B, that form a head-to-head symmetrical homodimer (FIG. 1C). To our knowledge, this arrangement of IL-37 subunits into a symmetrical homodimer is unique amongst structures of IL-1 family cytokines solved to date. The two subunits have a high degree of structural homology with a r.m.s. deviation of 0.70 Å over 142 Cα atoms. IL-37A is the most complete subunit, containing residues 48-207, with only residue 126 absent from the final map. Overall IL-37B has higher B-factors and is less complete, comprising residues 49-206 with residues 125-128, 161, and 194-196 missing from loop regions. The secondary structure of the p-trefoil fold begins at Lys58, and the N-terminal residues 48-57 are largely unstructured with electron density absent for residues 46-48. Two potential cleavage sites of mature IL-37 have been identified at residues 21 and 46, and based on the structure each are compatible with maintaining the p-trefoil fold of IL-37 after cleavage.

Each IL-37 subunit is composed of 12 β-strands and three α-helices that form the characteristic p-trefoil fold of the IL-1 superfamily (FIG. 1C). Three pseudorepeats of four p-strands pack together, with two strands from each repeat contributing to a six-stranded p-barrel and the remaining two strands to a six-stranded capping region. The interactions of the N- and C-terminal strands, β1 and β12, in the anti-parallel p-barrel closes the p-trefoil fold. Three α-helices decorate the outside of the p-trefoil fold, with helices α1 and α2 positioned between strand β7 and β8 with a short $3_{10}$ helix located after strand β11.

TABLE 3

Data collection and refinement statistics

| | IL-37(46-218) |
|---|---|
| Data collection | |
| Space group | P2₁2₁2 |
| Cell dimensions | |
| a, b, c (Å) | 59.58, 103.5, 77.53 |
| α, β, γ (°) | 90.0, 90.0, 90.0 |
| Resolution (Å) | 39.07-2.25 (2.37-2.25)* |
| $R_{merge}$ | 12.6 (134.1) |
| I/σI | 9.3 (1.3) |
| Completeness (%) | 99.2 (99.9) |
| Redundancy | 5.5 (5.6) |
| Refinement | |
| Resolution (Å) | 34.89-2.25 |
| No. reflections | 23157 |
| $R_{work}/R_{free}$ | 18.22/21.74 |
| No. atoms | |
| Protein | 2386 |
| Ligand/ion | 25 |
| Water | 158 |
| B-factors | |
| Protein | 59.17 |
| Ligand/ion | 93.70 |
| Water | 58.03 |
| R.m.s. deviations | |
| Bond lengths (Å) | 0.010 |
| Bond angles (°) | 1.09 |

*Values in parentheses are for highest-resolution shell and data-set is from a single crystal.

Figure 2A:
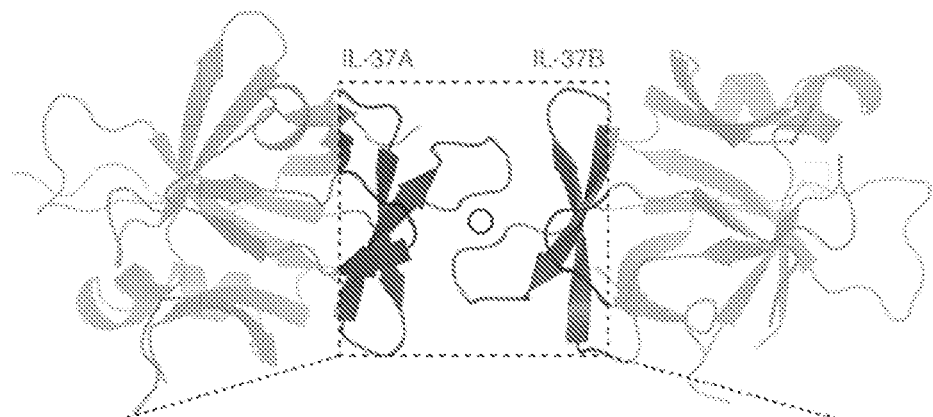
FIGS. 2A-D: Structural and mutational analysis of the IL-37 dimer interface.
Figure 2B:
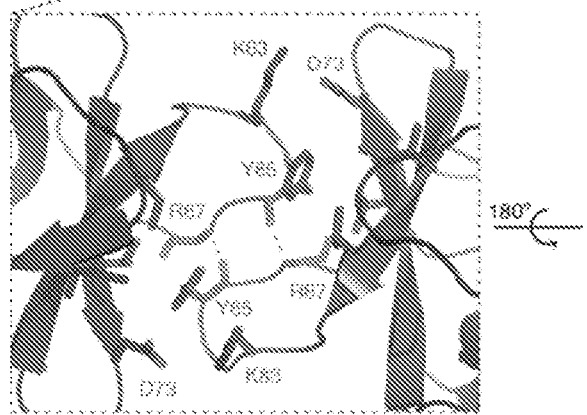
Figure 2C:
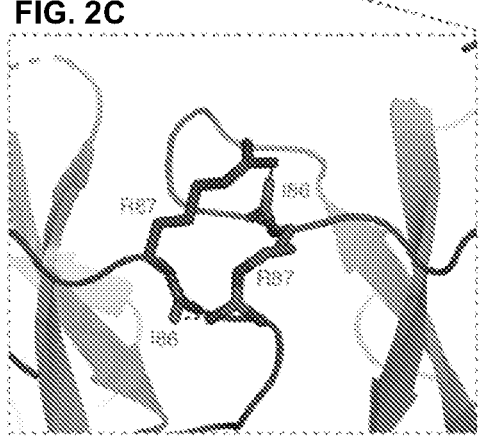

The IL-37 Homodimer has a Head-to-Head Symmetrical and Highly Organized Interface The symmetrical head-to-head IL-37 dimer interface buries a total of 487 Å² of surface area and is formed by the β3-β4 loops, and the three-stranded p-sheet (β2-β3-β11) of each subunit (FIG. 2A). The dimer interface appears highly organized, with numerous mirrored interactions forming across the $C_2$ symmetry axis centrally situated between the β3-β4 loop of each IL-37 subunit. Within the core of the interface, two main-chain hydrogen bonds are formed between Tyr85 and Arg87 from each IL-37 monomer (FIG. 2B). The partially hydrophobic Tyr85 side-chain of each subunit is buried in a hydrophobic pocket formed on the surface of the β2-β3-β11 β-sheet. This hydrophobic core of the interface is shielded by ionic interactions between Lys83 and Asp73 at the solvent exposed edges. Hydrogen bonds are also formed by the main chain carbonyl group of Ile86 and the side chain of Arg87 of each molecule, further strengthening the β3-β4 loop interface (FIG. 2C).

Figure 2D:
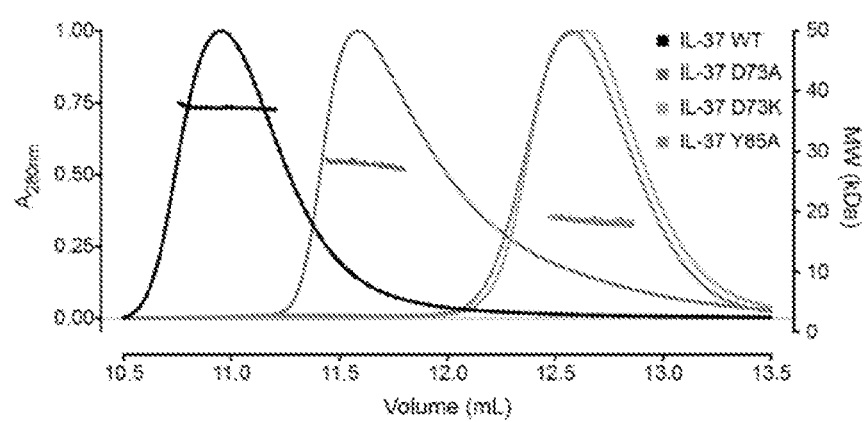

To validate the molecular details of the interface, and to generate monomeric IL-37, a number of structure-guided mutations were designed targeted to interfere with IL-37 dimerization. Asp73 forms ionic interactions with Lys83 within the interface, and a switched charge mutation at Asp73 (D73K) effectively ablated the interface, with a molecular mass of 18.8 kDa corresponding to an IL-37 monomer (FIG. 2D). Tyr85 is situated at the hydrophobic core and contributes a large buried surface area to the interface, and mutation to alanine (Y85A) also disrupted the dimer interface with a measured molecular weight of 18.2 kDa by SEC-MALS (FIG. 2D; IL-37 WT elutes at 11 ml, IL-37 D73A elutes at 11.6 ml, IL-37 D73K elute at 12.7 ml and IL-37 Y85A elutes at 12.6 ml). Due to the symmetry of the IL-37 dimer interface, each point mutation effectively targets two interaction sites in the interface and likely further assisted in the disruption of the dimer interface.

To asses alterations in the monomer-dimer interface five IL-37 mutants have currently been tested by SEC-MALS (FIG. 3; IL-37 D73A+K83A elutes at 11.1 ml, IL-37 K83E elutes at 11.6 ml, elution for other mutants and wildtype referred to above in relation to FIG. 2D) sits at the core of the interface and mutation to alanine (Y85A) converts IL-37 into a monomer. Asp73 sits at the boundary of the interface and forms ionic interactions with Lys83. Mutation of Asp73 to alanine (D73A) partially disrupts the dimer interface shifting the equilibrium towards the monomer. Switched charge mutation of Asp73 (D73K) ablates the dimer interface presumably by charge repulsion with Lys83. Switched charge mutation of Lys83 (K83E) shifted the equilibrium towards monomer but was not as effective as D73K at ablating the interface. Interestingly, complete removal of the ionic-interaction gating the interface (D73A/K83A) appears to have only minor effects on the equilibrium. These mutations suggest that the ionic gating interactions are not required for interface formation. Instead, the buried Tyr85 side-chain and hydrogen bonding of the β3-β4 loop region are likely more critical.

Example 3

Two approaches were used to assess the functional implications of IL-37 monomerization. First, fresh human PBMC were treated with different variants of recombinant (rec) IL-37, including the natural protein (wild-type), which dimerizes spontaneously even at very low concentrations, and the variant in which this dimerization is prevented by the D-to-K mutation of amino acid 73. Both of these variants were tested N-terminally truncated at amino acid 21 and 46.

As expected from previous studies, natIL-37 (wild-type recIL-37) conferred a moderate reduction in LPS-induced IL-1β protein (up to 40% by natIL-37 (21-218) and up to 52% by natIL-37 (46-218); FIG. 5, left group). Interestingly, increasing the concentration of natIL-37 to beyond 10 ng/ml, for example 100 ng/ml, strongly reduced natIL-37 effectiveness (FIG. 5); in fact, in three donors, 100 ng/ml natIL-37 (46-218) induced a pro-inflammatory response (up to 36% increase in IL-1β).

Monomerization of IL-37 markedly increased these anti-inflammatory activities. MonoIL-37 (D73K) was considerably more effective at blocking IL-1β release from LPS-treated PBMC than natIL-37 at all concentrations tested (FIG. 5). At 10 pg/ml, monoIL-37b (46-218) reduced IL-1β by 59%, a nearly 2-fold improvement over natIL-37 (46-218), and at 100 ng/ml monoIL-37 (46-218) was more than 5-fold more effective than natIL-37b (46-218). Moreover, monoIL-37b retained its anti-inflammatory activity at higher concentrations; hence, dimer formation likely contributes to reducing IL-37 activity at such concentrations or in fact converting it into a pro-inflammatory activity, as was the case with the 21-218 variants at 100 ng/ml (21% reduction in IL-1β by monoIL-37b compared to 26% increase in IL-1β by natIL-37). For monoIL-37 (46-218), the concentration range was further expanded, observing anti-inflammation at 1 pg/ml (52% reduction in IL-1β) and also at 1 pg/ml. Moreover, the loss of the anti-inflammatory functions occurred at a 10-fold higher concentration (1 pg/ml) than that of natIL-37. Remarkably, at the low end of the concentration range at 1 pg/ml, monomeric 46-218 recIL-37b was still 1.6-fold more active than 10 pg/ml of natural, dimeric recIL-37 (FIG. 5). N-terminal truncation also affected IL-37 function: the 46-218 variant was considerably more efficacious at blocking IL-1β production than the 21-218 variant comparing both, the natural as well as the D73K mutant with their counterparts (FIG. 5, group 1 vs group 3 and group 2 vs group 4; groups designated 1 to 4 from left to right).

To take IL-37's intracellular mechanism of action into account, the effect of IL 37 monomerization on its anti-inflammatory potency by transfection into THP-1 macrophages was assessed. Accordingly, a first comparison was made of the anti-inflammatory activity of dimeric natural IL-37b (natIL-37) with that of mutant monomeric IL-37b (D73K, monoIL-37) in THP-1 macrophages (FIG. 6). Transfection of full-length natIL-37 reduced LPS-induced IL-1β protein abundance by 71% compared to control transfection (271 to 80 pg/ml). The anti-inflammatory activity of monoIL-37 was 2.7-fold stronger, reducing IL-1β by 89% (271 to 30 pg/ml). Unlike natIL-37, monoIL-37 also decreased IL-1β in vehicle-treated cultures. These data demonstrate that the anti-inflammatory activity of monoIL-37 is greater than that of dimeric natIL-37, and that dimerization is not required for IL-37 bioactivity.

Protein abundance of TNF was also assessed in the supernatants of the PBMC and THP-1 cultures, revealing that IL-37 blocked this pro-inflammatory cytokine also, albeit with a somewhat lower efficacy than IL-1β (data not shown).

Example 4

In Vivo Model of Endotoxic Shock

To add the in vivo dimension to these findings, a mouse model of endotoxic shock was employed. C57Bl/6 wild-type mice received intraperitoneal injections of recombinant IL-37 variants (40 µg/kg) or vehicle, followed by intraperitoneal LPS injection. Mice transgenic for IL-37 were also treated with LPS or vehicle for direct comparison. Whereas each IL-37 variant ameliorated endotoxic shock (reducing hypothermia and plasma IL-1β, FIGS. 7 and 8), the anti-inflammatory activity of both monomeric IL-37 proteins was greater than that of their dimeric natIL-37 counterparts. Remarkably, the protection afforded by monoIL-37 (46-218) was nearly as strong as that conferred by the IL-37 transgene. Indeed, the difference between body temperature and plasma IL-1β in the monoIL-37 (46-218) group and that in mice which did not receive LPS was minimal.

Example 5

The mutation from tyrosine to alanine in position 85 is another approach (in addition to the D73K mutation) to disrupt the IL-37 dimer interface. The partially hydrophobic tyrosine residue at position 85 of each subunit is buried in a hydrophobic pocket formed by the dimer interface. Mutating this residue to alanine significantly decreases these interactions and disrupts the dimer interface. As such, recIL-37 Y85A is unable to form homodimers. Consistent with the concept of monomeric IL-37 possessing greater biological activity than dimeric IL-37b, the anti-inflammatory effects of recIL-37 Y85A were increased compared to recIL-37 D73K and particularly compared to natural recIL-37b in vitro in PBMC stimulated with the TLR2 agonist heat-killed Listeria monocytogenes (HKLM, FIG. 9) and in vivo in mice injected with the TLR4 agonist LPS (FIG. 7). However, in PBMC stimulated with the ligands of TLRs7 and -9, imiquimod and CpG-A respectively, there was little difference in biological activity between recIL-37 D73K and Y85A.

Overall, the data on the Y85A variant support the concept that, when used as an extracellular treatment, shifting the IL-37 monomer-to-dimer equilibrium towards the monomer increases the anti-inflammatory properties of IL-37.

Example 6

Effect of recIL-37 and Monomer Variants on Inflammation Induced by TLR Agonists Other than LPS

IL-37 acts as a powerful dampener of inflammation triggered by a wide spectrum of inflammatory assaults. In vitro, the inventors have shown that besides LPS, such assaults include the TLR1 agonist $Pam_3CSK_4$ (FIG. 1 in Nold et al, Nat Immunol 2010), IL-1β (FIGS. 3&4 in Nold et al, Nat Immunol 2010), LPS+IL-12, TNF and IL-12+IL-1β (FIG. 7 in Nold et al, Nat Immunol 2010 and FIG. 4 in Nold-Petry et al, Nat Immunol 2015). Moreover, IL-37 exerts protective effects in a large number of animal models of disease; besides the model of endotoxic shock, these include DSS colitis, harlequin ichthyosis, contact hypersensitivity and others.

Such activity against a broad range of inflammatory triggers is of high translational relevance, as it can therefore be expected that IL-37 will be efficacious in ameliorating inflammation in an equally broad spectrum of diseases, ranging from the common cold to psoriasis, myocardial infarction, stroke and many others.

However, the data described in Nold et al, Nat Immunol 2010 and Nold-Petry et al, Nat Immunol 2015 were generated either using cells transfected to express IL-37 or the mouse strain transgenic for IL-37. Since IL-37 possesses a dual mechanism of action, including an intracellular and an extracellular signalling pathway, it is important to establish that treatment with recIL-37, which likely acts nearly exclusively through the extracellular, IL-37 receptor-mediated pathway, is equally effective in blocking not only inflammation triggered by LPS, but also by other inflammatory agents. The data described herein show that this is indeed the case.

In human PBMC stimulated with the TLR2 agonist HKLM, recIL-37 conferred an up to 51% reduction in IL-1β and an up to 36% reduction IL-6 protein abundance (FIG. 9). The abundance of pro-inflammatory cytokines was also lower in cultures treated with the TLR7 ligand imiquimod+ recIL-37b (up to 36% less IL-1β, FIG. 10), the TLR9 agonist CpG-A+ recIL-37b (up to 30% less IL-6, FIG. 11), and ssRNA40 (up to 49% less IL-1β, FIG. 12), the ligand of TLR8.

Furthermore, the data herein strongly suggest that the anti-inflammatory effect of monomeric recIL-37 is greater than that of recIL-37 that is able to form homodimers. FIG. 5 shows that in PBMC stimulated with TLR4 ligand LPS, the monomeric D73K variant is significantly more active at most concentrations than its natural dimeric counterpart. In PBMC stimulated with ligands of TLRs 2 and 7, 8 and 9, there are similar observations: The Y85A variant was significantly more active than natural recIL-37 in blocking HKLM-(TLR 2 ligand) and imiquimod (TLR 7 ligand)-induced IL-1β or IL-6 (FIGS. 9 and 10, respectively). Moreover, the inhibition of IL-1β and IL-6 conferred by both D73K and Y85A was significant in imiquimod- and CpG-A (TLR 9 ligand)-stimulated cultures, whereas that conferred by natIL-37b was not (FIGS. 10 and 11, respectively). Although statistical analysis was not possible for the ligand of TLR8, ssRNA40, as only two donors were investigated, D73K was markedly more potent at blocking IL-1β than natIL-37 at each of the concentrations tested (FIG. 12).

The monomeric variants of IL-37 will be clinically efficacious as the active ingredient of drugs that block inflammation in wide variety of diseases caused by a broad spectrum of inflammatory insults.

REFERENCES

1. Nold, M. F., Nold-Petry, C. A., Zepp, J. A., Palmer, B. E., Bufler, P., and Dinarello, C. A. (2010) IL-37 is a fundamental inhibitor of innate immunity. *Nat. Immunol.* 11, 1014-1022
2. Kumar, S., Hanning, C. R., Brigham-Burke, M. R., Rieman, D. J., Lehr, R., Khandekar, S., Kirkpatrick, R. B., Scott, G. F., Lee, J. C., Lynch, F. J., Gao, W., Gambotto, A., and Lotze, M. T. (2002) Interleukin-1F7B (IL-1H4/IL-1F7) is processed by caspase-1 and mature IL-1F7B binds to the IL-1β receptor but does not induce IFN-gamma production. *Cytokine.* 18, 61-71
3. Kato, Z., Jee, J., Shikano, H., Mishima, M., Ohki, I., Ohnishi, H., Li, A., Hashimoto, K., Matsukuma, E., Omoya, K., Yamamoto, Y., Yoneda, T., Hara, T., Kondo, N., and Shirakawa, M. (2003) The structure and binding mode of interleukin-18. *Nat. Struct. Biol.* 10, 966-971
4. Tsutsumi, N., Kimura, T., Arita, K., Ariyoshi, M., Ohnishi, H., Yamamoto, T., Zuo, X., Maenaka, K., Park, E. Y., Kondo, N., Shirakawa, M., Tochio, H., and Kato, Z. (2014) The structural basis for receptor recognition of human interleukin-18. *Nat Commun.* 5, 5340
5. Nold-Petry, C. A., Lo, C. Y., Rudloff, I., Elgass, K. D., Li, S., Gantier, M. P., Lotz-Havla, A. S., Gersting, S. W., Cho, S. X., Lao, J. C., Ellisdon, A. M., Rotter, B., Azam, T., Mangan, N. E., Rossello, F. J., Whisstock, J. C., Bufler, P., Garlanda, C., Mantovani, A., Dinarello, C. A., and Nold, M. F. (2015) IL-37 requires the receptors IL-18Rα and IL-1R8 (SIGIRR) to carry out its multifaceted anti-inflammatory program upon innate signal transduction. *Nat. Immunol.* 16, 354-365 (2015).
6. Krissinel, E., and Henrick, K. (2007) Inference of macromolecular assemblies from crystalline state. *J. Mol. Biol.* 372, 774-797
7. Matsuura, Y., and Stewart, M. (2004) Structural basis for the assembly of a nuclear export complex. *Nature.* 432, 872-877
8. Collaborative Computational Project, Number 4 (1994) The CCP4 suite: programs for protein crystallography. *Acta Crystallogr. D Biol. Crystallogr.* 50, 760-763
9. Dunn, E. F., Gay, N. J., Bristow, A. F., Gearing, D. P., O'Neill, L. A. J., and Pei, X. Y. (2003) High-resolution structure of murine interleukin 1 homologue IL-1F5 reveals unique loop conformations for receptor binding specificity. *Biochemistry.* 42, 10938-10944
10. Bunkóczi, G., Echols, N., McCoy, A. J., Oeffner, R. D., Adams, P. D., and Read, R. J. (2013) Phaser.MRage: automated molecular replacement. *Acta Crystallogr. D Biol. Crystallogr.* 69, 2276-2286
11. Adams, P. D., Afonine, P. V., Bunkóczi, G., Chen, V. B., Davis, I. W., Echols, N., Headd, J. J., Hung, L.-W., Kapral, G. J., Grosse-Kunstleve, R. W., McCoy, A. J., Moriarty, N. W., Oeffner, R., Read, R. J., Richardson, D. C., Richardson, J. S., Terwilliger, T. C., and Zwart, P. H. (2010) PHENIX: a comprehensive Python-based system for macromolecular structure solution. *Acta Crystallogr. D Biol. Crystallogr.* 66, 213-221
12. BUSTER version 2.10.0
13. Emsley, P., and Cowtan, K. (2004) Coot: model-building tools for molecular graphics. *Acta Crystallogr. D Biol. Crystallogr.* 60, 2126-2132
14. Chen, V. B., Arendall, W. B., Headd, J. J., Keedy, D. A., Immormino, R. M., Kapral, G. J., Murray, L. W., Richardson, J. S., and Richardson, D. C. (2010) MolProbity: all-atom structure validation for macromolecular crystallography. *Acta Crystallogr. D Biol. Crystallogr.* 66, 12-21
15. Nold M., et al. IL-18BPa:Fc cooperates with immunosuppressive drugs in human whole blood. Biochem Pharmacol 66, 505-510 (2003).
16. Nold M. F., et al. Endogenous IL-32 Controls Cytokine and HIV-1 Production. J Immunol 181, 557-565 (2008).

The invention claimed is:

1. An anti-inflammatory polypeptide comprising an amino acid sequence of an IL-37 polypeptide,
   wherein the anti-inflammatory polypeptide has at least 95% sequence identity to the amino acid sequence of SEQ ID NO: 1 over the full length of SEQ ID NO: 1;
   wherein the anti-inflammatory polypeptide comprises a mutation or modification that reduces the capacity of the anti-inflammatory polypeptide to form a dimer, compared to a polypeptide comprising the amino acid sequence of SEQ ID NO: 1; and
   wherein the mutation or modification in the anti-inflammatory polypeptide is at any one or more residues, or residues equivalent to, 71 to 74, 78, 80, 83 to 88 and 184 in SEQ ID NO: 1,
   wherein the amino acid residue at, or equivalent to:
   position 71 in SEQ ID NO: 1 is not a Val;
   position 72 in SEQ ID NO: 1 is not an Leu;
   position 73 in SEQ ID NO: 1 is not a Asp;
   position 74 in SEQ ID NO: 1 is not a Ser;
   position 78 in SEQ ID NO: 1 is not an Ile;
   position 80 in SEQ ID NO: 1 is not a Val;
   position 83 in SEQ ID NO: 1 is not a Lys;
   position 84 in SEQ ID NO: 1 is not an Asn;
   position 85 in SEQ ID NO: 1 is not a Tyr;
   position 86 in SEQ ID NO: 1 is not an Ile;
   position 87 in SEQ ID NO: 1 is not an Arg;
   position 88 in SEQ ID NO: 1 is not a Pro; and/or
   position 184 in SEQ ID NO: 1 is not an Asn.

2. The anti-inflammatory polypeptide of claim 1, wherein the mutation prevents the anti-inflammatory polypeptide from forming a dimerization interface that enables dimerization of IL-37 monomers.

3. The anti-inflammatory polypeptide of claim 2, wherein the mutation is located in a region of the anti-inflammatory polypeptide that has the same amino acid sequence as the amino acid sequence that forms the dimerization interface of an IL-37 monomer.

4. The anti-inflammatory polypeptide of claim 3, wherein the mutation is located in the loop between the β3 and β4 strands that form the dimerization interface of an IL-37 monomer.

5. The anti-inflammatory polypeptide of claim 1, wherein the mutation or modification is located within a region, or a region equivalent to, residues 83 to 88 in SEQ ID NO:1.

6. The anti-inflammatory polypeptide according to claim 1, wherein the mutation or modification occurs at a residue at a position, or at a position equivalent to, D73, K83, N84, Y85, I86, R87 or P88 in SEQ ID NO: 1.

7. The anti-inflammatory polypeptide according to claim 1, wherein the mutation is a replacement with a non-conservative amino acid.

8. The anti-inflammatory polypeptide according to claim 1, wherein the mutation is replacement with alanine or an amino acid with an opposite charge.

9. The anti-inflammatory polypeptide according to claim 1, wherein the anti-inflammatory polypeptide has an amino acid sequence having at least 96%, 97%, 98% or 99% sequence identity with the amino acid sequence of SEQ ID NO: 1.

10. The anti-inflammatory polypeptide according to claim 1, wherein the mutation is any one or more of D73A, D73K, K83E and Y85A.

11. The anti-inflammatory polypeptide according to claim 1, wherein the mutation is D73A.

12. The anti-inflammatory polypeptide according to claim 1, wherein the mutation is D73K.

13. The anti-inflammatory polypeptide according to claim 1, wherein the mutation is K83E.

14. The anti-inflammatory polypeptide according to claim 1, wherein the mutation is Y85A.

15. The anti-inflammatory polypeptide according to claim 1, wherein one or more residues at a position, or position equivalent to, residues 83 to 88 of SEQ ID NO: 1 is deleted.

16. A pharmaceutical composition comprising the anti-inflammatory polypeptide according to claim 1 and a pharmaceutically acceptable diluent, excipient or carrier.

17. An anti-inflammatory polypeptide comprising an amino acid sequence of an IL-37 polypeptide,
wherein the polypeptide has an N terminal truncation of, or equivalent to, residues 1 to 20 or 1 to 45 of SEQ ID NO: 1,
wherein the polypeptide has at least 95% sequence identity to the amino acid sequence of 21 to 218 or 46 to 218 of SEQ ID NO: 1,
wherein the polypeptide comprises a mutation or modification that reduces the capacity of the anti-inflammatory polypeptide to form a dimer, compared to a polypeptide comprising the amino acid sequence of SEQ ID NO: 1; and
wherein the mutation or modification in the polypeptide is, or is equivalent to, any one or more of D73A, D73K, K83E and Y85A.

18. The anti-inflammatory polypeptide of claim 17, wherein the anti-inflammatory polypeptide has an amino acid sequence having at least 96% sequence identity to the amino acid sequence of 21 to 218 or 46 to 218 of SEQ ID NO: 1.

19. The anti-inflammatory polypeptide of claim 17, wherein the anti-inflammatory polypeptide has an amino acid sequence having at least 97% sequence identity to the amino acid sequence of 21 to 218 or 46 to 218 of SEQ ID NO: 1.

20. The anti-inflammatory polypeptide of claim 17, wherein the anti-inflammatory polypeptide has an amino acid sequence having at least 98% sequence identity to the amino acid sequence of 21 to 218 or 46 to 218 of SEQ ID NO: 1.

21. The anti-inflammatory polypeptide of claim 17, wherein the anti-inflammatory polypeptide has an amino acid sequence having at least 99% sequence identity to the amino acid sequence of 21 to 218 or 46 to 218 of SEQ ID NO: 1.

22. The anti-inflammatory polypeptide of claim 17, wherein the anti-inflammatory polypeptide has an amino acid sequence having at least 100% sequence identity to the amino acid sequence of 21 to 218 or 46 to 218 of SEQ ID NO: 1.

* * * * *